US006492138B1

(12) United States Patent
McGlade et al.

(10) Patent No.: US 6,492,138 B1
(45) Date of Patent: *Dec. 10, 2002

(54) POLYNUCLEOTIDES ENCODING A NOVEL SHC-BINDING PROTEIN

(75) Inventors: Jane McGlade; Rosemary Schmandt, both of Toronto (CA)

(73) Assignee: Amgen Canada Inc., Ontario (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,587

(22) Filed: May 21, 1998

(51) Int. Cl.$^7$ .................. C12P 21/06; C07H 21/04; C12N 1/21; C12N 5/10; C12N 15/63
(52) U.S. Cl. .................. 435/69.1; 435/6; 435/252.3; 435/252.31; 435/252.33; 435/252.34; 435/252.35; 435/320.1; 435/325; 435/348; 435/352; 435/358; 435/363; 435/365; 536/23.5; 536/24.31
(58) Field of Search .................. 435/6, 69.1, 252.3, 435/252.31, 252.33, 252.34, 252.35, 320.1, 325, 348, 352, 358, 363, 365; 536/23.5, 24.31

(56) References Cited

U.S. PATENT DOCUMENTS

| | | | | |
|---|---|---|---|---|
| 5,489,743 A | 2/1996 | Mak | ........................ | 800/2 |
| 5,557,032 A | 9/1996 | Robinson et al. | ........................ | 800/2 |
| 5,667,986 A | * 9/1997 | Goodey | ........................ | 435/69.1 |

FOREIGN PATENT DOCUMENTS

| | | |
|---|---|---|
| EP | 0 154 316 A2 | 9/1985 |
| EP | 0 401 384 A1 | 12/1990 |
| WO | WO 91/09955 | 7/1991 |
| WO | WO 92/20808 | 11/1992 |
| WO | WO 94/12650 | 6/1994 |
| WO | WO 94/28122 | 12/1994 |
| WO | WO 97/08314 | * 3/1997 |
| WO | WO 97/24440 | 7/1997 |

OTHER PUBLICATIONS

Burgess, W.H. et al. J. Cell Biology 111:2129, 1990.*
Lazar, E. et al. Mol. Cell. Biol. 8(3):1247–1252, 1988.*
Adams, M.D. et al. Nature Genetics 4:373–380, Aug. 1993.*
Adams, M.D. et al, Accession No. AA346160, Apr. 1997.*
Marra, M. et al, Accession No. AA265225, Mar. 1997.*
Hillier, L. et al, Accession No. AA401234, May 1997.*
Hillier, L. et al, Accession No. AA424274, Oct. 1997.*
Marra, M. et al, Accession No. AA530504, Jul. 1997.*
Hilbert, T.P. et al. J. Biol. Chem. 272(10):6733–6740, Mar. 1997.*
Sambrook, J. et al. Molecular cloning: a laboratory manual, 2nd edition, Cold Spring Harbor Laboratory Press, New York, p. 8.46–8.47; 8.60–8.63, 1989.*
Stratagene catalog, p. 21, 1993.*
Pharmacia catalog, p. 130, 1994.*
Anderson, D. et al., "Binding of SH2 Domains of Phospholipase $C_\gamma$ 1, GAP, and Src to Activated Growth Factor Receptors," *Science*, 250:979–982 (Nov. 16, 1990).
Aronheim, A. et al., "Membrane Targeting of the Nucleotide Exchange Factor Sos Is Sufficient for Activating the Ras Signaling Pathway," *Cell*, 78:949–961 (Sep. 23, 1994).
Bai, C. et al., "Gene Identification Using the Yeast TwoHybrid System," *Methods in Enzymology*, 273:331–347 (1996).
Blaikie, P. et al., "A Region in Shc Distinct from the SH2 Domain Can Bind Tyrosine–phosphorylated Growth Factor Receptors," *J. Biological Chemistry*, 269(51):32031–32034 (Dec. 23, 1994).
Bonfini, L. et al., "Not all Shc's roads lead to Ras," *TIBS*, 21:257–261 (Jul. 1996).
Buday, L. et al., "Epidermal Growth Factor Regulates $p21^{ras}$ through the Formation of a Complex of Receptor, Grb2 Adapter Protein, and Sos Nucleotide Exchange Factor," *Cell*, 73:611–620 (May 7, 1993).
Burns, L.A. et al., "Interleukin–2–induced Tyrosine Phosphorylation of $p52^{shc}$ in T Lymphocytes," *J. Biological Chemistry*, 268(24):17659–17661 (Aug. 25, 1993).
Cazaubon, S.M. et al., "Endothelin Induces Tyrosine Phosphorylation and GRB2 Association of Shc in Astrocytes," *J. Biological Chemistry*, 269(40):24805–24809 (Oct. 7, 1994).
Chardin, P. et al., "Human Sos1: A Guanine Nucleotide Exchange Factor for Ras That Binds to GRB2," *Science*, 260:1338–1343 (May 28, 1993).
Chen, Y. et al., "Shc adaptor proteins are key transducers of mitogenic signaling mediated by the G protein–coupled thrombin receptor," *EMBO J.*, 15(5):1037–1044 (1996).
Chien, C. et al., "The two–hybrid system: A method to identify and clone genes for proteins that interact with a protein of interest," *Proc. Natl. Acad. Sci., USA*, 88:9578–9582 (Nov. 1991).
Crowe, A.J. et al., "Phosphorylation of the SHC proteins on tyrosine correlates with the transformation of fibroblasts and erythroblasts by the v–sea tyrosine kinase," *Oncogene*, 9:537–544 (1994).
Cutler, R.L. et al., "Multiple Cytokines Induce the Tyrosine Phosphorylation of Shc and Its Association with Grb2 in Hemopoietic Cells," *J. Biological Chemistry*, 268(29):21463–21465 (Oct. 15, 1993).
Damen, J.E. et al., "Erythropoietin Stimulates the Tyrosine Phosphorylation of Shc and its Association With Grb2 and a 145–Kd Tyrosine Phosphorylation Protein," *Blood*, 82(8):2296–2303 (Oct. 15, 1993).

(List continued on next page.)

Primary Examiner—W. Gary Jones
Assistant Examiner—Diana Johannsen
(74) Attorney, Agent, or Firm—Marshall, Gerstein & Borun.

(57) ABSTRACT

Novel Shc-binding protein, oligonucleotides encoding the same, methods of producing and use thereof are disclosed.

17 Claims, 21 Drawing Sheets

OTHER PUBLICATIONS

Damen, J.E. et al., "The 145–kDa protein induced to associate with Shc by multiple cytokines is an inositol tetraphosphate and phosphatidylinositol 3,4,5–trisphosphate 5–phosphatase," *Proc. Natl. Acad. Sci., USA*, 93:1689–1693 (Feb. 1996).

DeChiara, T.M. et al., "Procedures for in Vitro DNA Mutagenesis of Human Leukocyte Interferon Sequences," *Methods in Enzymology*, 119:403–415 (1986).

Dikic, I. et al., "Shc Binding to Nerve Growth Factor Receptor Is Mediated by the Phosphotyrosine Interaction Domain," *J. Biological Chemistry*, 270(25):15125–15129 (Jun. 23, 1995).

Doyle, C. et al., "Analysis of Progressive Deletions of the Transmembrane and Cytoplasmic Domains of Influenza Hemagglutinin," *J. Cell Biology*, 103:1193–1204 (Oct. 1986).

Egan, S.E. et al., "Association of Sos Ras exchange protein with Grb2 is implicated in tyrosine kinase signal transduction and transformation," *Nature*, 363:45–51 (May 6, 1993).

Engels, J.W. et al., "*Gene Synthesis,*" *Angew. Chem. Int. Ed. Engl.*, 28:716–734 (1989).

Frohman, M.A. et al., "Rapid production of full–length cDNAs from rare transcripts: Amplification using a single gene–specific oligonucleotide primer," *Proc. Natl. Acad. Sci., USA*, 85: 8998–9002 (Dec. 1980).

Gotoh, N. et al., "A novel pathway from phosphorylation of tyrosine residues 239/240 of Shc, contributing to suppress apoptosis by IL–3," *EMBO J.*, 15(22):6197–6204 (1996).

Gotoh, N. et al., "Tyrosine Phosphorylation Sites at Amino Acids 239 and 240 of Shc Are Involved in Epidermal Growth Factor–Induced Mitogenic Signaling That Is Distinct from Ras/Mitogen–Activated Protein Kinase Activation," *Molecular and Cellular Biology*, 17(4):1824–1831 (Apr., 1997).

Harmer, S.L. et al. "Shc Contains Two Grb2 Binding Sites Needed for Efficient Formation of Complexes with SOS in B Lymphocytes," *Molecular and Cellular Biology*, 17(7):4087–4095 (Jul. 1997).

Houghten, R.A. et al., "General method for the rapid solid––phase synthesis of large numbers of peptides: Specificity of antigen–antibody interaction at the level of individual amino acids," *Proc. Natl. Acad. Sci., USA*, 82:5131–5135 (Aug. 1985).

Hwang, J. et al., "Functional Domains of Pseudomonas Exotoxin Identified by Deletion Analysis of the Gene Expressed in *E. coli*," *Cell*, 48:129–136 (Jan. 16, 1987).

Joung, I. et al., "Molecular cloning of a phosphotyrosine–independent ligand of the $p56^{lck}$ SH2 domain," *Proc. Natl. Acad. Sci., USA*, 93:5991–5995 (Jun. 1996).

Kavanaugh, W.M. et al., "Multiple forms of an inositol polyphosphate 5–phosphatase form signaling complexes with Shc and Grb2," *Current Biology*, 6(4):438–445 (1996).

Kozak, M., "Regulation Of Translation In Eukaryotic Systems," *Annu. Rev. Cell Biol.*, 8:197–225 (1992).

Lehmann, J.M. et al., "Nck, a melanoma cDNA encoding a cytoplasmic protein consisting of the src homology units SH2 and SH3," *Nucleic Acids Research*, 18(4):1048 (1990).

Li, N. et al., "Guanine–nucleotide–releasing factor hSos1 binds to Grb2 and links receptor tyrosine kinases to Ras signaling," *Nature*, 363:85–88 (May 6, 1993).

Lioubin, M.N. et al., "$p150^{Ship}$", a signal transduction molecule with inositol polyphosphate–5–phosphatase activity," *Genes & Development*, 10:1084–1095 (1996).

Lorenzo, M.J. et al., "RET alternate splicing influences the interaction of activated RET with the SH2 and PTB domains of Shc, and the SH2 domain of Grb2," *Oncogene*, 14:763–771 (1997).

Baldari, C.T. et al., "Inhibition of CD4/p56lck signaling by a dominant negative mutant of the Shc adaptor protein," *Oncogene*, 10:1141–1147 (1995).

Ma, J. et al. "Converting a Eukaryotic Transcriptional Inhibitor into an Activator," *Cell*, 51:443–446 (Nov. 4, 1988).

Mainiero, F. et al., "Signal transduction by the $α_6β_4$ integrin: distinct $β_4$ subunit sites mediate recruitment of Shc/Grb2 and association with the cytoskeleton of hemidesmosomes," *EMBO J.*, 14(8):4470–4481(1995).

Malek, S.N. et al., "A Cyclin–dependent Kinase Homologue, $p130^{PITSLRE}$, Is a Phosphotyrosine–independent SH2 Ligand," *J. Biological Chemistry*, 269(52):33009–33020 (Dec. 30, 1994).

Marengère, L.E.M. et al., "Regulation of T Cell Receptor Signaling by Tyrosine Phosphatase SYP Association with CTLA–4," *Science*, 272:1170–1173 (May 24, 1996).

Marengère, L.E.M. et al., "Proto–Oncoprotein Vav Interacts with c–Cbl in Activated Thymocytes and Peripheral T Cells," *J. Immunology*, 159:70–76 (1997).

Margolis, B. et al., "Tyrosine phosphorylation of vav proto–oncogene product containing SH2 domain and transcription factor motifs," *Nature*, 356: 71–74 (Mar. 5, 1992).

Marston, F.A.O. et al., "Solubilization of Protein Aggregates," *Methods in Enzymology*, 182:264–276 (1990).

Matoskova, B. et al., "Constitutive Phosphorylation of eps8 in Tumor Cell Lines: Relevance to Malignant Transformation," *Molecular and Cellular Biology*, 15(7):3805–3812 (Jul. 1995).

McBurney, M.W. et al., "Differentiation and Maturation of Embryonal Carcinoma–Derived Neurons in Cell Culture," *J. Neuroscience*, 8(3):1063–1073 (Mar., 1988).

McBurney, M.W. et al., "P19 embryonal carcinoma cells," *Int. J. Dev. Biol.*, 37(1):135–140 (Mar. 1993).

McGlade, C.J. et al., "SH2 Domains of the p85α Subunit of Phosphatidylinositol 3–Kinase Regulate Binding to Growth Factor Receptors," *Molecular and Cellular Biology*, 12(3):991–997 (Mar. 1992).

McGlade, J. et al., "Shc proteins are phosphorylated and regulated by the v–Src and v–Fps protein–tyrosine kinases," *Proc. Natl. Acad. Sci,. USA*, 89:8869–8873 (Oct. 1992).

Merrifield, R.B., "Solid Phase Peptide Synthesis. I. The Synthesis of a Tetrapeptide," *J. Am. Chem. Soc.*, 85:2149–2154 (1964).

Migliaccio, E. et al., "Opposite effects of the $p52^{shc}/p46^{shc}$ and $p66^{shc}$ splicing isoforms on the EGF receptor–MAP kinase–fos signaling pathway," *EMBO J.*, 16(4):706–716 (1997).

Miller, D.W. et al., "An Insect Baculovirus Host–Vector System For High–Level Expression Of Foreign Genes," *Genetic Engineering*, 8:277–298 (1986).

Obermeier, A. et al., "Neuronal differentiation signals are controlled by nerve growth factor receptor/Trk binding sites for SHC and PLCγ," *EMBO J.*, 13(7):1585–1590 (1994).

Pawson, T., "Protein modules and signaling networks," *Nature*, 373:573–579 (Feb. 16, 1995).

Pelicci, G. et al., "A Novel Transforming Protein (SHC) with an SH2 Domain Is Implicated in Mitogenic Signal Transduction," *Cell*, 70:93–104 (Jul. 10, 1992).

Pelicci, G. et al., "The motogenic and mitogenic responses to HGF are amplified by the Shc adaptor protein," *Oncogene*, 10:1631–1638 (1995).

Pelicci, G. et al., "Constitutive phosphorylation of Shc proteins in human tumors," *Oncogene*, 11:899–907 (1995).

Pendergast, A.M. et al., "BCR Sequences Essential for Transformation by the BCR–ABL Oncogene Bind to the ABL SH2 Regulatory Domain in a Non–Phosphotyrosine–Dependent Manner," *Cell*, 66:161–171 (Jul. 12, 1991).

Pronk, G.J. et al., "Insulin–induced Phosphorylation of the 46– and 52–kDa Shc Proteins," *J. Biological Chemistry*, 268(8):5748–5753 (Mar. 15, 1993).

Ptasznik, A. et al. "G Protein–coupled Chemoattractant Receptors Regulate Lyn Tyrosine Kinase–Shc Adaptor Protein Signaling Complexes," *J. Biological Chemistry*, 270(34):19969–19973 (Aug. 25, 1995).

Ravichandran, K.S. et al., "Interaction of Shc with the ζ Chain of the T Cell Receptor upon T Cell Activation," *Science*, 262:902–905 (Nov. 5, 1993).

Ravichandran, K.S. et al., "The Adaptor Protein Shc Interacts with the Interleukin–2 (IL–2) Receptor upon IL–2 Stimulation," *J. Biological Chemistry*, 269(3):1599–1602 (Jan. 21, 1994).

Ravichandran, K.S. et al., "Evidence for a role for the phosphotyrosine–binding domain of Shc in interleukin 2 signaling," *Proc. Natl. Acad. Sci., USA*, 93:5275–5280 (May 1996).

Rozakis–Adcock, M. et al., "Association of the Shc and Grb2/Sem5 SH2–containing proteins is implicated in activation of the Ras pathway by tyrosine kinases," *Nature*, 360:689–692 (Dec. 17, 1992).

Rozakis–Adcock, M. et al., "The SH2 and SH3 domains of mammalian Grb2 couple the EGF receptor to the Ras activator mSos1," *Nature*, 363:83–85 (May 6, 1993).

Rudnicki, M.A. et al. "Smooth Muscle Actin Expression During P19 Embryonal Carcinoma Differentiation in Cell Culture," *J. Cellular Physiology*, 142:89–98 (1990).

Salcini, A.E. et al., "Formation of Shc–Grb2 complexes is necessary to induce neoplastic transformation by overexpression of Shc proteins," *Oncogene*, 9:2827–2836 (1994).

Saxton, T.M. et al., "B Cell Antigen Receptor Cross–Linking Induced Phosphorylation of the $p21^{ras}$ Oncoprotein Activators SHC and mSOS1 As Well As Assembly of Complexes Containing SHC, GRB–2, mSOS1, and a 145–kDa Tyrosine–Phosphorylated Protein," *J. Immunology*, 153:623–636 (1994).

Segatto, O. et al., "Shc product are substrates of erbB–2 kinase," *Oncogene*, 8:2105–2112 (1993).

Songyang, Z. et al., "The phosphotyrosine Interaction Domain of SHC Recognizes Tyrosine–phosphorylated NPXY Motif," *J. Biological Chemistry*, 270(25):14863–14866 (Jun. 23, 1995).

Songyang, Z. et al., "Specific Motifs Recognized by the SH2 Domains of Csk, 3BP2, fps/fes, GRB–2, HCP, SHC, Syk, and Vav," *Molecular and Cellular Biology*, 14(4):2777–2785 (Apr. 1994).

Staudinger, J. et al., "Interactions among Vertebrate Helix-–Loop–Helix Proteins in Yeast Using the Two–hybrid System," *J. Biological Chemistry*, 268(7): 4608–4611 (Mar. 6, 1993).

Touhara, K. et al., "G protein βγ subunits stimulate phosphorylation of Shc adapter protein," *Proc. Natl. Acad. Sci., USA*, 92:9284–9287 (Sep. 1995).

van Biesen, T. et al., "Receptor–tyrosine–kinase– and Gβγ–mediated MAP kinase activation by a common signaling pathway," *Nature*, 376:781–784 (Aug. 31, 1995).

van der Geer, P. et al., "Receptor Protein–Tyrosine Kinases And Their Signal Transduction Pathways," *Ann. Rev. Cell Biol.*, 10:251–337 (1994).

van der Geer, P. et al., "The Shc adaptor protein is highly phosphorylated at conserved, twin tyrosine residues (Y239/240) that mediate protein–protein interactions," *Current Biology*, 6(11):1435–1444 (1996).

Waterhouse, P. et al., "Lymphoproliferative Disorders with Early Lethality in Mice Deficient in Ctla–4," *Science*, 270:985–988 (Nov. 10, 1995).

Wary, K.K. et al., "The Adaptor Protein Shc Couples a Class of Integrins to the Control of Cell Cycle Progression," *Cell*, 87:733–743 (Nov. 15, 1996).

Waye, M.M.Y. et al., "Deletion mutagenesis using an 'M13 splint': the N–terminal structural domain of tyrosyl–tRNA synthetase (*B. stearothermophilus*) catalyses the formation of tyrosyl adenylate," *EMBO J.*, 2(10):1827–1829 (1983).

Yokote, K. et al., "Direct Interaction between Shc and the Platelet–derived Growth Factor β–Receptor," *J. Biological Chemistry*, 269(21):15337–15343 (May 27, 1994).

Zumstein, L. et al., "Probing the Structural Domains and Function in Vivo of *Escherichia coli* DNA Topoisomerase I by Mutagenesis," *J. Mol. Biol.*, 191:333–340 (1986).

Frohman, M.A., "RACE: Rapid Amplification of cDNA Ends," in *PCR Protocols: A Guide to Methods and Amplifications*, Innis et al. (Eds.), Academic Press, Inc., pp. 28–38 (1990).

Higuchi, R., "Recombinant PCR," in *PCR Protocols: A Guide to Methods and Applications*, Innis et al. (Eds.), Academic Press, Inc., pp. 177–183 (1990).

Janeway, C.A. et al. Immunobiology: The Immune System in Health and Disease, Current Biology Ltd., London, 1994, p. 2:3, 1994.*

* cited by examiner hPAL cDNA

```
GGATCCGCGG GAAATTTGAA ATGGCTGACG GGTCGCTGAC GGGCGGGCGGT CTGGAGGCAG    60
CGGCCATGGC GCCGGAGCGC ACGGGCTGGG CGGTGGAGCA CGGTGGAGCG TCTCTGGAGA   120
AAGGTTTGTT CCAAGATGAA GATTCATGCA GTGATTGTAG CTACCGTGAT AAACCAGGTT   180
CTAGTTTACA AAGTTTTATG CCAGAAGGAA AAACCTTTTT CCCAGAAATT TTCCAAACAA   240
ATCAACTTTT GTTCTATGAG CGATTCAGAG CCTATCAAGA TTACATTTTA GCTGACTGCA   300
AGGCCTCTGA GGTACAGGAA TTCACACAGCTG AGTTCTTGGA GAAGGTCCTT GAGCCATCTG   360
GATGGGCGGGC AGTCTGGCAC ACTAATGTGT TCAAGGTGCT GGTTGAGATC ACAGATGTGG   420
ACTTTGCAGC CTTGAAGGCA GTGGGTGAGGC TTGCTGAACC ATACCCTCTGT GACTCTCAAG   480
TGAGCACTTT TACCATGGAG TGCATGAAGG AGCTCCTTGA TCTGAAGGAG CATCGGGTTGC   540
CCCTGCAGGA GCTGTGGGTG GTGTTTGATG ATTCAGGAGT GTTTGACCAG ACAGCCCTTG   600
CAATTGAGCA TGTCAGATTT TTCTACCAAA ACATTTGGGAG GAGTTGGGAT GAAGAAGAGG   660
AGGATGAATA CGATTATTTT GTCAGATGTG TTGAACCCTCG ATTAAGATTG CATTATGACA   720
```

FIG 1A hPAL cDNA

```
TTCTTGAAGA CCGAGTTCCA TCAGGACTTA TTGTTGACTA CCACAATCTG TTGTCTCAAT  780
GTGAGGAGAG TTACAGGAAA TTTTTAAATC TGAGAAGCAG TTTGTCAAAT TGTAACTCTG  840
ATTCCGAGCA GGAAAATATC TCCATGGTGG AAGGGTTAAA ATTGTATTCG GAGATGGAAC  900
AGTTGAAACA AAAGCTGAAA CTCATTGAGA ATCCTTTGTT GAGGTATGTG TTTGGTTATC  960
AGAAGAATTC TAACATCCAA GCAAAGGGTG TCCGTTCCAG CGGTCAGAAG ATCACTCATG 1020
TGGTCTCCTC CACCATGATG GCTGGTCTCC TGCGGTCCCT GCTTACGGAC AGGCTTTGCC 1080
AGGAGCCTGG TGAGGAAGAA AGAGAAATTC AGTTCCATAG TGATCCATTG TCTGCTATAA 1140
ATGCCTGCTT CGAAGGTGAC ACTGTTATTG TTTGTCCTGG CCATTATGTG GTACATGGCA 1200
CTTTCTCCAT TGCTGACTCC ATTGAGTTGG AAGGATATGG CCTACCAGAT GACATTGTGA 1260
TAGAAAAGAG GGGCAAAGGC GACACTTTTG TGGACTGCAC TGGTGCTGAT ATTAAAATCT 1320
CAGGCATAAA ATTGTTCAG CATGATGCTG TAGAGGGAAT CTTAATTGTT CACCGTGGTA 1380
AGACTACGCT GGAAAACTGT GTGCTGCAGT GTGAGACGAC CGGAGTCACA GTGCGGACAT 1440
```

FIG 1B hPAL cDNA

```
CAGCAGAGTT TCTAATGAAG AACTCGGATT TATATGGCGC CAAGGGTGCT GGTATAGAAA   1500
TCTACCCTGG GAGTCAGTGC ACCCTGAGTG ACAATGGGAT CCATCACTGC AAGGAAGGGA   1560
TCCTCATTAA GGACTTCTTA GATGAACATT ATGACATTCC CAAGATATCC ATGGTGAATA   1620
ATATAATACA TAATAATGAA GGTTATGGTG TTGTCTTGGT GAAACCTACA ATCTTCTCTG   1680
ACCTGCAAGA AAATGCTGAA GATGGAACTG AAGAAAATAA AGCGCTTAAA ATTCAGACAA   1740
GTGGAGAGCC AGATGTGGCT GAAAGAGTGG ATCTAGAGGA GCTGATTAAG TGTGCAACTG   1800
GTAAAATGGA GCTTTGTGCA AGAACTGACC CTTCTGAGCA AGTCGAGGGA AATTGTGGAA   1860
TTGTAAATGA ACTAATTGCT GCCTCCACAC AGAAAGGCCA GATAAAGAAG AAAAGGTTGA   1920
GTGAACTGGG GATCACGCAA GCTGATGACA ACTTAATGTC ACAGGAGATG TTTGTTGGGA   1980
TTGTGGGGAA CCAGTTCAAG TGGAATGGGA AAGGTAGTTT TGGCACATTT CTTTTCTGAC   2040
TACAGTGATG CAAGTAGATA GCAAAATACT GGATTTTGCA CATGCTGCCC TAAGAATCAC   2100
TGCTGCCATT GTAGTTGCT GTATTGTCTG TATTTATAT TTGATTATTT GGGCTTGAGT   2160
```

FIG 1C hPAL cDNA

```
GAAAGGTAGA TTTATTCCA TTTGCAGGTG TTGCACATAA AACACTCCCT CTTTATAAGA    2220
AAAATCATAA ATGCATATAA AATAGAAAAT ATTTGGAGAT TGCTTATCTG AAAGTCTTGC    2280
TTTCTTATAC ACATGGTTCT CTCATATTAA GCCTGGTGGT AACTTTTTAG TGTAATTACC    2340
TTTAGCACTT CAAAGACGAG GAAGTAAGGA AGGGAATGCA AGACTAGTGC ATAAAAATGC    2400
AATAGGTGTC ATATGTACAG CATTCTTCTT AGAGTTGCCT CTTGTCTTAA ATAAAAGCT    2460
GTCTGATTTC CATCCTGTAT TTGCATAATA CTTGTCTTAA AATAAAAGCT TTTATGATTG    2520
GGGAAAAAAA AAAAAAAAAA GGAAAAAAAA AAAAAAAAAA AAAAAAAAAA AAAAAAAAAA    2580
A
```

FIG. 1D hPAL PEPTIDE

```
Met Ala Asp Gly Ser Leu Thr Gly Gly Leu Glu Ala Ala Ala Met
 1                   5                  10                  15
Ala Pro Glu Arg Thr Gly Trp Ala Val Glu Gln Glu Leu Ala Ser Leu
              20                  25                  30
Glu Lys Gly Leu Phe Gln Asp Glu Asp Ser Cys Ser Asp Cys Ser Tyr
             35                  40                  45
Arg Asp Lys Pro Gly Ser Ser Leu Gln Ser Phe Met Pro Glu Gly Lys
             50                  55                  60
Thr Phe Phe Pro Glu Ile Phe Gln Thr Asn Gln Leu Leu Phe Tyr Glu
 65                  70                  75                  80
Arg Phe Arg Ala Tyr Gln Asp Tyr Ile Leu Ala Asp Cys Lys Ala Ser
              85                  90                  95
Glu Val Gln Glu Phe Thr Ala Glu Phe Leu Glu Lys Val Leu Glu Pro
            100                 105                 110
Ser Gly Trp Arg Ala Val Trp His Thr Asn Val Phe Lys Val Leu Val
            115                 120                 125
```

FIG. 2A hPAL PEPTIDE

Glu Ile Thr Asp Val Asp Phe Ala Ala Leu Lys Ala Val Val Arg Leu
130                     135                     140
Ala Glu Pro Tyr Leu Cys Asp Ser Gln Val Ser Thr Phe Thr Met Glu
145                     150                     155                 160
Cys Met Lys Glu Leu Leu Asp Leu Lys Glu His Arg Leu Pro Leu Gln
165                     170                     175
Glu Leu Trp Val Val Phe Asp Asp Ser Gly Val Phe Asp Gln Thr Ala
180                     185                     190
Leu Ala Ile Glu His Val Arg Phe Phe Tyr Gln Asn Ile Trp Arg Ser
195                     200                     205
Trp Asp Glu Glu Glu Asp Glu Tyr Asp Tyr Phe Val Arg Cys Val
210                     215                     220
Glu Pro Arg Leu Arg Leu His Tyr Asp Ile Leu Glu Asp Arg Val Pro
225                     230                     235                 240
Ser Gly Leu Ile Val Asp Tyr His Asn Leu Leu Ser Gln Cys Glu Glu
245                     250                     255

FIG2B hPAL PEPTIDE

Ser Tyr Arg Lys Phe Leu Asn Leu Arg Ser Ser Leu Ser Asn Cys Asn
260                                    265                                   270

Ser Asp Ser Glu Gln Glu Asn Ile Ser Met Val Glu Gly Leu Lys Leu
275                                    280                                   285

Tyr Ser Glu Met Glu Gln Leu Lys Gln Lys Leu Lys Leu Ile Glu Asn
290                                    295                                   300

Pro Leu Arg Tyr Val Phe Gly Tyr Gln Lys Asn Ser Asn Ile Gln
305                                    310                                   315                  320

Ala Lys Gly Val Arg Ser Ser Gly Gln Lys Ile Thr His Val Val Ser
325                                    330                                   335

Ser Thr Met Met Ala Gly Leu Leu Arg Ser Leu Leu Thr Asp Arg Leu
340                                    345                                   350

Cys Gln Glu Pro Gly Glu Glu Arg Glu Ile Gln Phe His Ser Asp
355                                    360                                   365

Pro Leu Ser Ala Ile Asn Ala Cys Phe Glu Gly Asp Thr Val Ile Val
370                                    375                                   380

FIG. 2C hPAL PEPTIDE

Cys Pro Gly His Tyr Val Val His Gly Thr Phe Ser Ile Ala Asp Ser
385                          390                         395                         400
Ile Leu Glu Gly Tyr Gly Leu Pro Asp Asp Ile Val Ile Glu Lys
                 405                         410                         415
Arg Gly Lys Gly Asp Thr Phe Val Asp Cys Thr Gly Ala Asp Ile Lys
                 420                         425                         430
Ile Ser Gly Ile Lys Phe Val Gln His Asp Ala Val Glu Gly Ile Leu
                 435                         440                         445
Ile Val His Arg Gly Lys Thr Thr Leu Glu Asn Cys Val Leu Gln Cys
                 450                         455                         460
Glu Thr Thr Gly Val Thr Val Arg Thr Ser Ala Glu Phe Leu Met Lys
465                          470                         475                         480
Asn Ser Asp Leu Tyr Gly Ala Lys Gly Ala Lys Gly Ile Glu Ile Tyr Pro
                 485                         490                         495
Gly Ser Gln Cys Thr Leu Ser Asp Asn Gly Ile His His Cys Lys Glu
                 500                         505                         510

FIG 2D hPAL PEPTIDE

Gly Ile Leu Ile Lys Asp Phe Leu Asp Glu His Tyr Asp Ile Pro Lys
515                     520                     525

Ile Ser Met Val Asn Asn Ile Ile His Asn Asn Glu Gly Tyr Gly Val
530                     535                     540

Val Leu Val Lys Pro Thr Ile Phe Ser Asp Leu Gln Glu Asn Ala Glu
545                     550                     555                     560

Asp Gly Thr Glu Glu Asn Lys Ala Leu Lys Ile Gln Thr Ser Gly Glu
565                     570                     575

Pro Asp Val Ala Glu Arg Val Asp Leu Glu Glu Leu Ile Glu Cys Ala
580                     585                     590

Thr Gly Lys Met Glu Leu Cys Ala Arg Thr Asp Pro Ser Glu Gln Val
595                     600                     605

Glu Gly Asn Cys Glu Ile Val Asn Glu Leu Leu Ile Ala Ala Ser Thr Gln
610                     615                     620

Lys Gly Gln Ile Lys Lys Arg Leu Ser Gly Leu Gly Ile Thr Gln
625                     630                     635                     640

FIG 2E hPAL PEPTIDE

Ala Asp Asp Asn Leu Met Ser Gln Glu Met Phe Val Gly Ile Val Gly
                645                 650                 655

Asn Gln Phe Lys Trp Asn Gly Lys Gly Ser Phe Gly Thr Phe Leu Phe
                660                 665                 670

FIG 2F

MOUSE PAL cDNA

```
GTAAATTTGA AATGGCTGAT GATTTGCGGG CTGGTTGGAGT TCTGGAACCT ATAGCTATGG    60
TTCCACCGAG ACCTGACTTG GCGGCGGAGA AGGAACCGGC GTCCTGGAAG GAAGGTTTAT   120
TCTTGGATGC AGATCCATGC AGTGATCAAG GCTATCATGC TAATCCAGGT GCTACTGTAA   180
AAACTCTCAT ACCAGAAGGA AAAACTCCTT TTCCACGAAT TATCCAAACA AATGAACTTC   240
TGTTTTATGA ACGATTCAGA GCCTATCAAG ATTACATTTT AGCTGACTGT AAGGCCTCTG   300
AGGTAAAGGA ATTCACAGTC AGCTTCTTGG AAAAGGTCCT TGAACCATCT GGATGGTGGG   360
CAGTCTGGCA CACTAATGTG TTTGAGGTGT TGGTTGAGGT TACAAATGTG GACTTTCCAT   420
CCCTGAAGGC GGTCGTAAGG CTTGCAGAGC CATGCATCTA TGAATCTAAA TTGAGCACGT   480
TTACCTTGGC CAATGTGAAG GAGCTTTTGG ACCTGAAGGA GTTTCATCTG CCTCTGCAGG   540
AGTTGTGGGT GGTATCAGAT GACTCACATG AATTCCACCA GATGGCACTT GCAATTGAGC   600
ACGTCAGATT TTTCTACAAA CACATCTGGA GGAGTTGGGA TGAGGAAGAG GAGGATGAGT   660
ATGACTATTT TGTCAGATGT GTTGAACCTC GACTGAGATT GTATTATGAC ATACTTGAAG   720
ATCGAGTTCC CTCGGGACTT ATTGTTGACT ACCACAATCT GTTGTCTCAA TGTGAAGAGA   780
GTTACAGGAA ATTTTTAAAT CTGAGAAGCA GTTGTCCAA TTGTAATTCT GATTCTGAGC   840
```

FIG 3A

MOUSE PAL cDNA

```
AGGAAAATAT CTCCATGGTG GAAGGGTTAA ATTTGTATTC AGAAATTGAA CAGTTGAAAC   900
AAAAGCTAAA GCTCATTGAG AATCCTTTGT TAAGATATGT TTTTGGTTAT CAGAAGAACT   960
CTAATATCCA AGGAAAGGGT ACTCGTCAAA ATGGCCAGAA GGTCATCCAT GTGGTTTCCT  1020
CCACCATGAA GACAGGTCTA CTTCGGTCTC TATTCAAGGA CAGGTTTTGT GAGGAGTCTT  1080
GCAAAGAAGA AACAGAAATT AAGTTCCATA GTGATCTGTT GTCTGGTATA AATGCCTGCT  1140
ATGATGGTGA CACTGTTCATT ATTTGTCCTG GCCATTATGT AGTTCATGGC ACCTGTTCCA  1200
TAGCTGACTC CATTGAGTTG GAAGGATATG GCCTACCAGA TGACATTGTC ATAGAAAAGA  1260
GGGGCAAAGG AGATACTTTT GTGGATTGCA CGGGTATGGA TGTTAAAATT TCAGGCATAA  1320
AATTATTCA GCATGATTCT GTGGAAGGAA TCTTAATCAT TCACCATGGC AAGACCACAC  1380
TGGAAAACTG TGTACTACAA TGTGAAACCA CAGGAGTCAC AGTGCCGCACA TCAGCAGAAC  1440
TTTTCATGAA AAACTCAGAT GTATATGGTG CCAAGGGTGC TGGTATAGAA ATATATCCTG  1500
GAAGTAAATG TACCCTGACT GACAATGGAA TCCATCACTG CAAGGAAGGA ATTCTCATTA  1560
AGGACTTCCT TGATGAACAT TATGATATTC CCAAAATATC GATGATAAAT AACGTCATAC  1620
ACAATAATGA AGGTTATGGT GTTGTTTGG TGAAGCCTAC AATTTTCTGT GATCTACAGG  1680
```

FIG 3B

MOUSE PAL cDNA

```
AAATACACA AGATGAAATT AATGACAATA TGGTTCAGAA AATAAAGAG GCAGATGTCA   1740
CTGAAGGATT AGATCTGGAA GAAATGCTTC AGTGTGTGGC TAGCAAAATG GAGCCTTATG  1800
CCACAGCTGA CTTTAATGAA CAAGCTAAGG GAAACTGTGA AATTATAAAT GAACTACTTG  1860
CTATTTCCAT GCAAAAAGGC CGGATGAAGA AAAGACTGAG TGAACTTGGG ATTACACAAG  1920
CTGATGACAA CATAATGTCA CAGGAGATGT TTATTGAAAT TATGGGGAAC CAGTTTAAGT  1980
GGAATGGCAA AGGGAGTTTT GGCACATTTC TTTACTAGCT ACAATAATAT CAATACTCAC  2040
AAAATACTGT ATTTGAACA TGTCTTAAGT ATGCTGCTTA TATACTTTGC TTCATTTGCT  2100
TCATGGCTGT GTATTATATA AAGTGTACTT GACCAAAAAA AAAAAAAAAA AAAAAAAAAA  2160
AAAAAAAAAA AAAAAAAAAA AAAAAAAAAA AAAAAAAAAA AAAAAAAAAA AAAAAAAAAA  2220
AAAAAAAAAA AAAAAAAAAA AAAAAA                                      2246
```

FIG 3C

MOUSE PAL PEPTIDE

MET ALA ASP ASP LEU ARG ALA GLY GLY VAL LEU GLU PRO ILE ALA MET
1                5                   10                  15

VAL PRO PRO ARG PRO ASP LEU ALA ALA GLU LYS GLU PRO ALA SER TRP
            20                  25                  30

LYS GLU GLY LEU PHE LEU ASP ALA ASP PRO CYS SER ASP GLN GLY TYR
            35                  40                  45

HIS ALA ASN PRO GLY ALA THR VAL LYS THR LEU ILE PRO GLU GLY LYS
            50                  55                  60

THR PRO PHE PRO ARG ILE ILE GLN THR ASN GLU LEU LEU PHE TYR GLU
65                  70                  75                  80

ARG PHE ARG ALA TYR GLN ASP TYR ILE LEU ALA ASP CYS LYS ALA SER
                85                  90                  95

GLU VAL LYS GLU PHE THR VAL SER PHE LEU GLU LYS VAL LEU GLU PRO
            100                 105                 110

SER GLY TRP TRP ALA VAL TRP HIS THR ASN VAL PHE GLU VAL LEU VAL
            115                 120                 125

GLU VAL THR ASN VAL ASP PHE PRO SER LEU LYS ALA VAL VAL ARG LEU
130                 135                 140

FIG. 4A

MOUSE PAL PEPTIDE

Ala Glu Pro Cys Ile Tyr Glu Ser Lys Leu Ser Thr Phe Thr Leu Ala
145                 150                 155                 160

Asn Val Lys Glu Leu Leu Asp Leu Lys Glu Phe His Leu Pro Leu Gln
        165                 170                 175

Glu Leu Trp Val Val Ser Asp Asp Ser His Glu Phe His Gln Met Ala
        180                 185                 190

Leu Ala Ile Glu His Val Arg Phe Phe Tyr Lys His Ile Trp Arg Ser
        195                 200                 205

Trp Asp Glu Glu Glu Asp Glu Tyr Asp Tyr Phe Val Arg Cys Val
210                 215                 220

Glu Pro Arg Leu Arg Leu Tyr Tyr Asp Ile Leu Glu Asp Arg Val Pro
225                 230                 235                 240

Ser Gly Leu Ile Val Asp Tyr His Asn Leu Leu Ser Gln Cys Glu Glu
        245                 250                 255

Ser Tyr Arg Lys Phe Leu Asn Leu Arg Ser Ser Leu Ser Asn Cys Asn
        260                 265                 270

Ser Asp Ser Glu Gln Glu Asn Ile Ser Met Val Glu Gly Leu Asn Leu
275                 280                 285

FIG 4B

MOUSE PAL PEPTIDE

Tyr Ser Glu Ile Glu Gln Leu Lys Gln Lys Leu Lys Leu Ile Glu Asn
    290                 295                 300                 320?

Pro Leu Arg Tyr Val Phe Gly Tyr Gln Lys Asn Ser Asn Ile Gln
    305                 310                 315                 320

Gly Lys Gly Thr Arg Gln Asn Gly Gln Lys Val Ile His Val Val Ser
            325                 330                 335

Ser Thr Met Lys Thr Gly Leu Leu Arg Ser Leu Phe Lys Asp Arg Phe
            340                 345                 350

Cys Glu Ser Cys Lys Glu Ile Glu Thr Glu Thr Glu Lys Phe His Ser Asp
    355                 360                 365

Leu Leu Ser Gly Ile Asn Ala Cys Tyr Asp Gly Asp Thr Val Ile Ile
    370                 375                 380

Cys Pro Gly His Tyr Val Val His Gly Thr Cys Ser Ile Ala Asp Ser
    385                 390                 395                 400

Ile Glu Leu Glu Gly Tyr Gly Leu Pro Asp Asp Ile Val Ile Lys
    405                 410                 415

Arg Gly Lys Gly Asp Thr Phe Val Asp Cys Thr Gly Met Asp Val Lys
    420                 425                 430

FIG 4C

MOUSE PAL PEPTIDE

Ile Ser Gly Ile Lys Phe Ile Gln His Asp Ser Val Glu Gly Ile Leu
435                 440                 445

Ile Ile His His Gly Lys Thr Thr Leu Glu Asn Cys Val Leu Gln Cys
450                 455                 460

Glu Thr Thr Gly Val Thr Val Arg Thr Ser Ala Glu Leu Phe Met Lys
465                 470                 475                 480

Asn Ser Asp Val Tyr Gly Ala Lys Gly Ala Gly Ile Glu Ile Tyr Pro
485                 490                 495

Gly Ser Lys Cys Thr Leu Thr Asp Asn Gly Ile His His Cys Lys Glu
500                 505                 510

Gly Ile Leu Ile Lys Asp Phe Leu Asp Glu His Tyr Asp Ile Pro Lys
515                 520                 525

Ile Ser Met Ile Asn Asn Val Ile His Asn Asn Glu Gly Tyr Gly Val
530                 535                 540

Val Leu Val Lys Pro Thr Ile Phe Cys Asp Leu Gln Glu Asn Thr Gln
545                 550                 555                 560

Asp Glu Ile Asn Asp Asn Met Val Gln Lys Asn Lys Glu Ala Asp Val
565                 570                 575

FIG 4D

MOUSE PAL PEPTIDE

Thr Glu Gly Leu Asp Leu Glu Glu Met Leu Gln Cys Val Ala Ser Lys
                580                 585                 590

Met Glu Pro Tyr Ala Thr Ala Asp Phe Asn Glu Gln Ala Lys Gly Asn
                595                 600                 605

Cys Glu Ile Ile Asn Glu Leu Leu Ala Ile Ser Met Gln Lys Gly Arg
                610                 615                 620

Met Lys Lys Arg Leu Ser Glu Leu Gly Ile Leu Thr Gln Ala Asp Asp Asn
                625                 630                 635                 640

Ile Met Ser Gln Glu Met Phe Ile Glu Ile Met Gly Asn Gln Phe Lys
                645                 650                 655

Trp Asn Gly Lys Gly Ser Phe Gly Thr Phe Leu Tyr
                660                 665

FIG. 4E

AMINO ACID ALIGNMENT OF HUMAN AND MOUSE PAL

```
HUMAN PAL   ---GSLT--G ---AA---A-E- TGW-V-Q-L- -LEK---Q-E -S---CS-RD
MOUSE PAL   ---DLRA--V -PI--V-P- PDL-A-K-P- -WKE---L-A -P---QG-HA 100
51
HUMAN PAL   K--SSLQSFM ------F--E- F---Q----- ---------- -------Q--
MOUSE PAL   N--ATVKTLI ------P--R- I---E----- ---------- -------K--

150
101
HUMAN PAL   --AE------ ------R---- ---K---I -D----AA--- ------YLC
MOUSE PAL   --VS------ ------W---- ---E---V -N----PS--- ------CIY 200
151
HUMAN PAL   D-QV----ME CM------ HR-------- -F---GV-D- T---------
MOUSE PAL   E-KL----LA NV------ FH-------- -S---HE-H- M---------

250
201
HUMAN PAL   --QN------ ---------- H--------- ---------- ----------
MOUSE PAL   --KH------ ---------- Y--------- ---------- ----------

300
251
HUMAN PAL   ---------- ---------- ---------- ----K--- -M--------
MOUSE PAL   ---------- ---------- ---------- ----N--- -I--------
```

FIG 5A

AMINO ACID ALIGNMENT OF HUMAN AND MOUSE PAL

```
              301                                                      350
HUMAN PAL     ---------- ---------- ---------- A--V-SS--- IT-----M A-----LT-
MOUSE PAL     ---------- ---------- ---------- G--T-QN--- VI-----K T-----FK- 351                                                      400
HUMAN PAL     -L-Q-PGE-- R--Q----P- -A----FE-- ---V------ ------F -------
MOUSE PAL     -F-E-SCK-- T--K----L- -G----YD-- ---I------ ------C -------

401                                                      450
HUMAN PAL     ---------- ---------- ---------- ----A----- I----V- --A---V
MOUSE PAL     ---------- ---------- ---------- ----M----- V----I- --S---I 451                                                      500
HUMAN PAL     -R-------- ---------- ---------- ----FL---- ---L-- -Q-
MOUSE PAL     -H-------- ---------- ---------- ----LF---- ---V-- -K-

501                                                      550
HUMAN PAL     -S-------- ---------- ---------- ---------- ---Y-I- -----
MOUSE PAL     -T-------- ---------- ---------- ---------- ---I--V -----

551                                                      600
HUMAN PAL     -S-----AE -GTEE---K I-TSG-P--A -RV----LIE -ATG---LC-
MOUSE PAL     -C-----TQ -EIND---M V-KNK-A--T -GL----MLQ -VAS---PY- 601                                                      650
HUMAN PAL     RT-PS--VE- ---V--I- A-T---QI- ---------- ----L----- ---------
MOUSE PAL     TA-FN--AK- ---I--L- I-M---RM- ---------- ----I----- ---------
```

FIG 5B

AMINO ACID ALIGNMENT OF HUMAN AND MOUSE PAL

```
HUMAN PAL   -VG-V---- -------- -F*
MOUSE PAL   -IE-M---- -------- -Y~
```

FIG 5C

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 2581 base pairs
      (B) TYPE: nucleic acid
      (C) STRANDEDNESS: single
      (D) TOPOLOGY: linear (ii) MOLECULE TYPE: cDNA
      (A) DESCRIPTION: /desc = "hPAL cDNA"

(xi) SEQUENCE DESCRIPTION: SEQ ID NO:1:

```
GGATCCGCGG GAAATTTGAA ATGGCTGACG GGTCGCTGAC GGGCGGCGGT CTGGAGGCAG      60

CGGCCATGGC GCCGGAGCGC ACGGGCTGGG CGGTGGAGCA GGAGCTGGCG TCTCTGGAGA     120

AAGGTTTGTT CCAAGATGAA GATTCATGCA GTGATTGTAG CTACCGTGAT AAACCAGGTT     180

CTAGTTTACA AAGTTTTATG CCAGAAGGAA AAACCTTTTT CCCAGAAATT TTCCAAACAA     240

ATCAACTTTT GTTCTATGAG CGATTCAGAG CCTATCAAGA TTACATTTTA GCTGACTGCA     300

AGGCCTCTGA GGTACAGGAA TTCACAGCTG AGTTCTTGGA GAAGGTCCTT GAGCCATCTG     360

GATGGCGGGC AGTCTGGCAC ACTAATGTGT TCAAGGTGCT GGTTGAGATC ACAGATGTGG     420

ACTTTGCAGC CTTGAAGGCA GTGGTGAGGC TTGCTGAACC ATACCTCTGT GACTCTCAAG     480

TGAGCACTTT TACCATGGAG TGCATGAAGG AGCTCCTTGA TCTGAAGGAG CATCGGTTGC     540

CCCTGCAGGA GCTGTGGGTG GTGTTTGATG ATTCAGGAGT GTTTGACCAG ACAGCCCTTG     600

CAATTGAGCA TGTCAGATTT TTCTACCAAA ACATTTGGAG GAGTTGGGAT GAAGAAGAGG     660

AGGATGAATA CGATTATTTT GTCAGATGTG TTGAACCTCG ATTAAGATTG CATTATGACA     720

TTCTTGAAGA CCGAGTTCCA TCAGGACTTA TTGTTGACTA CCACAATCTG TTGTCTCAAT     780

GTGAGGAGAG TTACAGGAAA TTTTTAAATC TGAGAAGCAG TTTGTCAAAT TGTAACTCTG     840

ATTCCGAGCA GGAAAATATC TCCATGGTGG AAGGGTTAAA ATTGTATTCG GAGATGGAAC     900
```

-continued

| | |
|---|---|
| AGTTGAAACA AAAGCTGAAA CTCATTGAGA ATCCTTTGTT GAGGTATGTG TTTGGTTATC | 960 |
| AGAAGAATTC TAACATCCAA GCAAAGGGTG TCCGTTCCAG CGGTCAGAAG ATCACTCATG | 1020 |
| TGGTCTCCTC CACCATGATG GCTGGTCTCC TGCGGTCCCT GCTTACGGAC AGGCTTTGCC | 1080 |
| AGGAGCCTGG TGAGGAAGAA AGAGAAATTC AGTTCCATAG TGATCCATTG TCTGCTATAA | 1140 |
| ATGCCTGCTT CGAAGGTGAC ACTGTTATTG TTTGTCCTGG CCATTATGTG GTACATGGCA | 1200 |
| CTTTCTCCAT TGCTGACTCC ATTGAGTTGG AAGGATATGG CCTACCAGAT GACATTGTGA | 1260 |
| TAGAAAAGAG GGGCAAAGGC GACACTTTTG TGGACTGCAC TGGTGCTGAT ATTAAAATCT | 1320 |
| CAGGCATAAA ATTTGTTCAG CATGATGCTG TAGAGGGAAT CTTAATTGTT CACCGTGGTA | 1380 |
| AGACTACGCT GGAAAACTGT GTGCTGCAGT GTGAGACGAC CGGAGTCACA GTGCGGACAT | 1440 |
| CAGCAGAGTT TCTAATGAAG AACTCGGATT TATATGGCGC CAAGGGTGCT GGTATAGAAA | 1500 |
| TCTACCCTGG GAGTCAGTGC ACCCTGAGTG ACAATGGGAT CCATCACTGC AAGGAAGGGA | 1560 |
| TCCTCATTAA GGACTTCTTA GATGAACATT ATGACATTCC CAAGATATCC ATGGTGAATA | 1620 |
| ATATAATACA TAATAATGAA GGTTATGGTG TTGTCTTGGT GAAACCTACA ATCTTCTCTG | 1680 |
| ACCTGCAAGA AAATGCTGAA GATGGAACTG AAGAAAATAA AGCGCTTAAA ATTCAGACAA | 1740 |
| GTGGAGAGCC AGATGTGGCT GAAAGAGTGG ATCTAGAGGA GCTGATTAAG TGTGCAACTG | 1800 |
| GTAAAATGGA GCTTTGTGCA AGAACTGACC CTTCTGAGCA AGTCGAGGGA AATTGTGGAA | 1860 |
| TTGTAAATGA ACTAATTGCT GCCTCCACAC AGAAAGGCCA GATAAAGAAG AAAAGGTTGA | 1920 |
| GTGAACTGGG GATCACGCAA GCTGATGACA ACTTAATGTC ACAGGAGATG TTTGTTGGGA | 1980 |
| TTGTGGGGAA CCAGTTCAAG TGGAATGGGA AAGGTAGTTT TGGCACATTT CTTTTCTGAC | 2040 |
| TACAGTGATG CAAGTAGATA GCAAAATACT GGATTTTGCA CATGCTGCCC TAAGAATCAC | 2100 |
| TGCTGCCATT GTAGTTTGCT GTATTGTCTG TATTTTATAT TTGATTATTT GGGCTTGAGT | 2160 |
| GAAAGGTAGA TTTATTTCCA TTTGCAGGTG TTGCACATAA AACACTCCCT CTTTATAAGA | 2220 |
| AAAATCATAA ATGCATATAA AATAGAAAAT ATTTGGAGAT TGCTTATCTG AAAGTCTTGC | 2280 |
| TTTCTTATAC ACATGGTTCT CTCATATTAA GCCTGGTGGT AACTTTTTAG TGTAATTACC | 2340 |
| TTTAGCACTT CAAAGACGAG GAAGTAAGGA AGGGAATGCA AGACTAGTGC ATAAAAATGC | 2400 |
| AATAGGTGTC ATATGTACAG CATTCTTCTT AGAGTTGCCT TTTCATCCCA ATTACAGTGA | 2460 |
| GTCTGATTTC CATCCTGTAT TTGCATAATA CTTGTCTTAA AATAAAAGCT TTTATGATTG | 2520 |
| GGGAAAAAAA AAAAAAAAAA GGAAAAAAAA AAAAAAAAAA AAAAAAAAAA AAAAAAAAAA | 2580 |
| A | 2581 |

(2) INFORMATION FOR SEQ ID NO:2:

(i) SEQUENCE CHARACTERISTICS:
        (A) LENGTH: 672 amino acids
        (B) TYPE: amino acid
        (C) STRANDEDNESS: Not Relevant
        (D) TOPOLOGY: linear (ii) MOLECULE TYPE: peptide
        (A) DESCRIPTION: /desc = "hPAL peptide"

(xi) SEQUENCE DESCRIPTION: SEQ ID NO:2:

```
Met Ala Asp Gly Ser Leu Thr Gly Gly Gly Leu Glu Ala Ala Ala Met
1               5                   10                  15

Ala Pro Glu Arg Thr Gly Trp Ala Val Glu Gln Glu Leu Ala Ser Leu
            20                  25                  30

Glu Lys Gly Leu Phe Gln Asp Glu Asp Ser Cys Ser Asp Cys Ser Tyr
```

-continued

```
            35                  40                  45
Arg Asp Lys Pro Gly Ser Ser Leu Gln Ser Phe Met Pro Glu Gly Lys
 50                  55                  60

Thr Phe Pro Glu Ile Phe Gln Thr Asn Gln Leu Leu Phe Tyr Glu
 65                  70                  75                  80

Arg Phe Arg Ala Tyr Gln Asp Tyr Ile Leu Ala Asp Cys Lys Ala Ser
                     85                  90                  95

Glu Val Gln Glu Phe Thr Ala Glu Phe Leu Glu Lys Val Leu Glu Pro
                100                 105                 110

Ser Gly Trp Arg Ala Val Trp His Thr Asn Val Phe Lys Val Leu Val
                115                 120                 125

Glu Ile Thr Asp Val Asp Phe Ala Ala Leu Lys Ala Val Val Arg Leu
         130                 135                 140

Ala Glu Pro Tyr Leu Cys Asp Ser Gln Val Ser Thr Phe Thr Met Glu
145                 150                 155                 160

Cys Met Lys Glu Leu Leu Asp Leu Lys Glu His Arg Leu Pro Leu Gln
                165                 170                 175

Glu Leu Trp Val Val Phe Asp Asp Ser Gly Val Phe Asp Gln Thr Ala
                180                 185                 190

Leu Ala Ile Glu His Val Arg Phe Phe Tyr Gln Asn Ile Trp Arg Ser
             195                 200                 205

Trp Asp Glu Glu Glu Asp Glu Tyr Asp Tyr Phe Val Arg Cys Val
         210                 215                 220

Glu Pro Arg Leu Arg Leu His Tyr Asp Ile Leu Glu Asp Arg Val Pro
225                 230                 235                 240

Ser Gly Leu Ile Val Asp Tyr His Asn Leu Leu Ser Gln Cys Glu Glu
                245                 250                 255

Ser Tyr Arg Lys Phe Leu Asn Leu Arg Ser Ser Leu Ser Asn Cys Asn
                260                 265                 270

Ser Asp Ser Glu Gln Glu Asn Ile Ser Met Val Glu Gly Leu Lys Leu
         275                 280                 285

Tyr Ser Glu Met Glu Gln Leu Lys Gln Lys Leu Lys Leu Ile Glu Asn
         290                 295                 300

Pro Leu Leu Arg Tyr Val Phe Gly Tyr Gln Lys Asn Ser Asn Ile Gln
305                 310                 315                 320

Ala Lys Gly Val Arg Ser Ser Gly Gln Lys Ile Thr His Val Val Ser
                325                 330                 335

Ser Thr Met Met Ala Gly Leu Leu Arg Ser Leu Leu Thr Asp Arg Leu
             340                 345                 350

Cys Gln Glu Pro Gly Glu Glu Arg Glu Ile Gln Phe His Ser Asp
         355                 360                 365

Pro Leu Ser Ala Ile Asn Ala Cys Phe Glu Gly Asp Thr Val Ile Val
370                 375                 380

Cys Pro Gly His Tyr Val Val His Gly Thr Phe Ser Ile Ala Asp Ser
385                 390                 395                 400

Ile Glu Leu Glu Gly Tyr Gly Leu Pro Asp Asp Ile Val Ile Glu Lys
                405                 410                 415

Arg Gly Lys Gly Asp Thr Phe Val Asp Cys Thr Gly Ala Asp Ile Lys
                420                 425                 430

Ile Ser Gly Ile Lys Phe Val Gln His Asp Ala Val Glu Gly Ile Leu
         435                 440                 445

Ile Val His Arg Gly Lys Thr Thr Leu Glu Asn Cys Val Leu Gln Cys
450                 455                 460
```

```
Glu Thr Thr Gly Val Thr Val Arg Thr Ser Ala Glu Phe Leu Met Lys
465                 470                 475                 480

Asn Ser Asp Leu Tyr Gly Ala Lys Gly Ala Gly Ile Glu Ile Tyr Pro
                485                 490                 495

Gly Ser Gln Cys Thr Leu Ser Asp Asn Gly Ile His His Cys Lys Glu
            500                 505                 510

Gly Ile Leu Ile Lys Asp Phe Leu Asp Glu His Tyr Asp Ile Pro Lys
            515                 520                 525

Ile Ser Met Val Asn Asn Ile Ile His Asn Asn Glu Gly Tyr Gly Val
        530                 535                 540

Val Leu Val Lys Pro Thr Ile Phe Ser Asp Leu Gln Glu Asn Ala Glu
545                 550                 555                 560

Asp Gly Thr Glu Glu Asn Lys Ala Leu Lys Ile Gln Thr Ser Gly Glu
                565                 570                 575

Pro Asp Val Ala Glu Arg Val Asp Leu Glu Glu Leu Ile Glu Cys Ala
            580                 585                 590

Thr Gly Lys Met Glu Leu Cys Ala Arg Thr Asp Pro Ser Glu Gln Val
            595                 600                 605

Glu Gly Asn Cys Glu Ile Val Asn Glu Leu Ile Ala Ala Ser Thr Gln
610                 615                 620

Lys Gly Gln Ile Lys Lys Lys Arg Leu Ser Glu Leu Gly Ile Thr Gln
625                 630                 635                 640

Ala Asp Asp Asn Leu Met Ser Gln Glu Met Phe Val Gly Ile Val Gly
                645                 650                 655

Asn Gln Phe Lys Trp Asn Gly Lys Gly Ser Phe Gly Thr Phe Leu Phe
                660                 665                 670
```

(2) INFORMATION FOR SEQ ID NO:3:

(i) SEQUENCE CHARACTERISTICS:
        (A) LENGTH: 2246 base pairs
        (B) TYPE: nucleic acid
        (C) STRANDEDNESS: single
        (D) TOPOLOGY: linear (ii) MOLECULE TYPE: cDNA
        (A) DESCRIPTION: /desc = "mouse PAL cDNA"

(xi) SEQUENCE DESCRIPTION: SEQ ID NO:3:

```
GTAAATTTGA AATGGCTGAT GATTTGCGGG CTGGTGGAGT TCTGGAACCT ATAGCTATGG    60

TTCCACCGAG ACCTGACTTG GCGGCGGAGA AGGAACCGGC GTCCTGGAAG GAAGGTTTAT   120

TCTTGGATGC AGATCCATGC AGTGATCAAG GCTATCATGC TAATCCAGGT GCTACTGTAA   180

AAACTCTCAT ACCAGAAGGA AAAACTCCTT TTCCACGAAT TATCCAAACA AATGAACTTC   240

TGTTTTATGA ACGATTCAGA GCCTATCAAG ATTACATTTT AGCTGACTGT AAGGCCTCTG   300

AGGTAAAGGA ATTCACAGTC AGCTTCTTGG AAAAGGTCCT TGAACCATCT GGATGGTGGG   360

CAGTCTGGCA CACTAATGTG TTTGAGGTGT TGGTTGAGGT TACAAATGTG ACTTTCCAT   420

CCCTGAAGGC GGTCGTAAGG CTTGCAGAGC CATGCATCTA TGAATCTAAA TTGAGCACGT   480

TTACCTTGGC CAATGTGAAG GAGCTTTTGG ACCTGAAGGA GTTTCATCTG CCTCTGCAGG   540

AGTTGTGGGT GGTATCAGAT GACTCACATG AATTCCACCA GATGGCACTT GCAATTGAGC   600

ACGTCAGATT TTTCTACAAA CACATCTGGA GGAGTTGGGA TGAGGAAGAG GAGGATGAGT   660

ATGACTATTT TGTCAGATGT GTTGAACCTC GACTGAGATT GTATTATGAC ATACTTGAAG   720

ATCGAGTTCC CTCGGGACTT ATTGTTGACT ACCACAATCT GTTGTCTCAA TGTGAAGAGA   780
```

-continued

```
GTTACAGGAA ATTTTTAAAT CTGAGAAGCA GTTTGTCCAA TTGTAATTCT GATTCTGAGC      840

AGGAAAATAT CTCCATGGTG GAAGGGTTAA ATTTGTATTC AGAAATTGAA CAGTTGAAAC      900

AAAAGCTAAA GCTCATTGAG AATCCTTTGT TAAGATATGT TTTTGGTTAT CAGAAGAACT      960

CTAATATCCA AGGAAAGGGT ACTCGTCAAA ATGGCCAGAA GGTCATCCAT GTGGTTTCCT     1020

CCACCATGAA GACAGGTCTA CTTCGGTCTC TATTCAAGGA CAGGTTTTGT GAGGAGTCTT     1080

GCAAAGAAGA AACAGAAATT AAGTTCCATA GTGATCTGTT GTCTGGTATA AATGCCTGCT     1140

ATGATGGTGA CACTGTCATT ATTTGTCCTG GCCATTATGT AGTTCATGGC ACCTGTTCCA     1200

TAGCTGACTC CATTGAGTTG GAAGGATATG GCCTACCAGA TGACATTGTC ATAGAAAAGA     1260

GGGGCAAAGG AGATACTTTT GTGGATTGCA CGGGTATGGA TGTTAAAATT TCAGGCATAA     1320

AATTTATTCA GCATGATTCT GTGGAAGGAA TCTTAATCAT TCACCATGGC AAGACCACAC     1380

TGGAAAACTG TGTACTACAA TGTGAAACCA CAGGAGTCAC AGTGCGCACA TCAGCAGAAC     1440

TTTTCATGAA AAACTCAGAT GTATATGGTG CCAAGGGTGC TGGTATAGAA ATATATCCTG     1500

GAAGTAAATG TACCCTGACT GACAATGGAA TCCATCACTG CAAGGAAGGA ATTCTCATTA     1560

AGGACTTCCT TGATGAACAT TATGATATTC CCAAAATATC GATGATAAAT AACGTCATAC     1620

ACAATAATGA AGGTTATGGT GTTGTTTTGG TGAAGCCTAC AATTTTCTGT GATCTACAGG     1680

AAAATACACA AGATGAAATT AATGACAATA TGGTTCAGAA AAATAAAGAG GCAGATGTCA     1740

CTGAAGGATT AGATCTGGAA GAAATGCTTC AGTGTGTGGC TAGCAAAATG GAGCCTTATG     1800

CCACAGCTGA CTTTAATGAA CAAGCTAAGG GAAACTGTGA AATTATAAAT GAACTACTTG     1860

CTATTTCCAT GCAAAAAGGC CGGATGAAGA AAAGACTGAG TGAACTTGGG ATTACACAAG     1920

CTGATGACAA CATAATGTCA CAGGAGATGT TTATTGAAAT TATGGGGAAC CAGTTTAAGT     1980

GGAATGGCAA AGGGAGTTTT GGCACATTTC TTTACTAGCT ACAATAATAT CAATACTCAC     2040

AAAATACTGT ATTTTGAACA TGTCTTAAGT ATGCTGCTTA TATACTTTGC TTCATTTGCT     2100

TCATGGCTGT GTATTATATA AAGTGTACTT GACCAAAAAA AAAAAAAAAA AAAAAAAAAA     2160

AAAAAAAAAA AAAAAAAAAA AAAAAAAAAA AAAAAAAAAA AAAAAAAAAA AAAAAAAAAA     2220

AAAAAAAAAA AAAAAAAAAA AAAAA                                          2246
```

(2) INFORMATION FOR SEQ ID NO:4:

(i) SEQUENCE CHARACTERISTICS:
        (A) LENGTH: 668 amino acids
        (B) TYPE: amino acid
        (C) STRANDEDNESS: Not Relevant
        (D) TOPOLOGY: linear (ii) MOLECULE TYPE: peptide
        (A) DESCRIPTION: /desc = "mouse PAL peptide"

(xi) SEQUENCE DESCRIPTION: SEQ ID NO:4:

```
Met Ala Asp Asp Leu Arg Ala Gly Gly Val Leu Glu Pro Ile Ala Met
1               5                  10                  15

Val Pro Pro Arg Pro Asp Leu Ala Ala Glu Lys Glu Pro Ala Ser Trp
            20                  25                  30

Lys Glu Gly Leu Phe Leu Asp Ala Asp Pro Cys Ser Asp Gln Gly Tyr
        35                  40                  45

His Ala Asn Pro Gly Ala Thr Val Lys Thr Leu Ile Pro Glu Gly Lys
    50                  55                  60

Thr Pro Phe Pro Arg Ile Ile Gln Thr Asn Glu Leu Leu Phe Tyr Glu
65                  70                  75                  80
```

-continued

```
Arg Phe Arg Ala Tyr Gln Asp Tyr Ile Leu Ala Asp Cys Lys Ala Ser
             85                  90                  95
Glu Val Lys Glu Phe Thr Val Ser Phe Leu Glu Lys Val Leu Glu Pro
            100                 105                 110
Ser Gly Trp Trp Ala Val Trp His Thr Asn Val Phe Glu Val Leu Val
            115                 120                 125
Glu Val Thr Asn Val Asp Phe Pro Ser Leu Lys Ala Val Val Arg Leu
            130                 135                 140
Ala Glu Pro Cys Ile Tyr Glu Ser Lys Leu Ser Thr Phe Thr Leu Ala
145                 150                 155                 160
Asn Val Lys Glu Leu Leu Asp Leu Lys Glu Phe His Leu Pro Leu Gln
            165                 170                 175
Glu Leu Trp Val Val Ser Asp Asp Ser His Glu Phe His Gln Met Ala
            180                 185                 190
Leu Ala Ile Glu His Val Arg Phe Phe Tyr Lys His Ile Trp Arg Ser
            195                 200                 205
Trp Asp Glu Glu Glu Glu Asp Glu Tyr Asp Tyr Phe Val Arg Cys Val
            210                 215                 220
Glu Pro Arg Leu Arg Leu Tyr Tyr Asp Ile Leu Glu Asp Arg Val Pro
225                 230                 235                 240
Ser Gly Leu Ile Val Asp Tyr His Asn Leu Leu Ser Gln Cys Glu Glu
            245                 250                 255
Ser Tyr Arg Lys Phe Leu Asn Leu Arg Ser Ser Leu Ser Asn Cys Asn
            260                 265                 270
Ser Asp Ser Glu Gln Glu Asn Ile Ser Met Val Glu Gly Leu Asn Leu
            275                 280                 285
Tyr Ser Glu Ile Glu Gln Leu Lys Gln Lys Leu Lys Leu Ile Glu Asn
290                 295                 300
Pro Leu Leu Arg Tyr Val Phe Gly Tyr Gln Asn Ser Asn Ile Gln
305                 310                 315                 320
Gly Lys Gly Thr Arg Gln Asn Gly Gln Lys Val Ile His Val Val Ser
            325                 330                 335
Ser Thr Met Lys Thr Gly Leu Leu Arg Ser Leu Phe Lys Asp Arg Phe
            340                 345                 350
Cys Glu Glu Ser Cys Lys Glu Glu Thr Glu Ile Lys Phe His Ser Asp
            355                 360                 365
Leu Leu Ser Gly Ile Asn Ala Cys Tyr Asp Gly Asp Thr Val Ile Ile
            370                 375                 380
Cys Pro Gly His Tyr Val Val His Gly Thr Cys Ser Ile Ala Asp Ser
385                 390                 395                 400
Ile Glu Leu Glu Gly Tyr Gly Leu Pro Asp Asp Ile Val Ile Glu Lys
            405                 410                 415
Arg Gly Lys Gly Asp Thr Phe Val Asp Cys Thr Gly Met Asp Val Lys
            420                 425                 430
Ile Ser Gly Ile Lys Phe Ile Gln His Asp Ser Val Glu Gly Ile Leu
            435                 440                 445
Ile Ile His His Gly Lys Thr Thr Leu Glu Asn Cys Val Leu Gln Cys
450                 455                 460
Glu Thr Thr Gly Val Thr Val Arg Thr Ser Ala Glu Leu Phe Met Lys
465                 470                 475                 480
Asn Ser Asp Val Tyr Gly Ala Lys Gly Ala Gly Ile Glu Ile Tyr Pro
            485                 490                 495
```

```
Gly Ser Lys Cys Thr Leu Thr Asp Asn Gly Ile His His Cys Lys Glu
            500                 505                 510
Gly Ile Leu Ile Lys Asp Phe Leu Asp Glu His Tyr Asp Ile Pro Lys
            515                 520                 525
Ile Ser Met Ile Asn Asn Val Ile His Asn Asn Glu Gly Tyr Gly Val
            530                 535                 540
Val Leu Val Lys Pro Thr Ile Phe Cys Asp Leu Gln Glu Asn Thr Gln
545                 550                 555                 560
Asp Glu Ile Asn Asp Asn Met Val Gln Lys Asn Lys Glu Ala Asp Val
                    565                 570                 575
Thr Glu Gly Leu Asp Leu Glu Glu Met Leu Gln Cys Val Ala Ser Lys
                    580                 585                 590
Met Glu Pro Tyr Ala Thr Ala Asp Phe Asn Glu Gln Ala Lys Gly Asn
            595                 600                 605
Cys Glu Ile Ile Asn Glu Leu Leu Ala Ile Ser Met Gln Lys Gly Arg
610                 615                 620
Met Lys Lys Arg Leu Ser Glu Leu Gly Ile Thr Gln Ala Asp Asp Asn
625                 630                 635                 640
Ile Met Ser Gln Glu Met Phe Ile Glu Ile Met Gly Asn Gln Phe Lys
                    645                 650                 655
Trp Asn Gly Lys Gly Ser Phe Gly Thr Phe Leu Tyr
            660                 665
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Met Val Pro Pro Arg Pro Asp Leu Ala Ala Glu Lys Glu Pro
1               5                   10
```

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Phe Leu Val Arg Glu Ser
1               5
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "outer primer"

(xi) SEQUENCE DESCRIPTION: SEQ ID NO:7:

```
CCTCAGGGAC CTTGCAGTCA GCTA                                              24
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "nested primer"

(xi) SEQUENCE DESCRIPTION: SEQ ID NO:8:

```
CTTTCTCCAG AGACGCCAGC TCCT                                              24
```

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "outer primer"

(xi) SEQUENCE DESCRIPTION: SEQ ID NO:9:

```
GACTACGCTG GAAAACTGTG TGCT                                              24
```

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "nested primer"

(xi) SEQUENCE DESCRIPTION: SEQ ID NO:10:

```
ATGGGATCCA TCACTGCAAG GAAG                                              24
```

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "5' mutagenic primer"

(xi) SEQUENCE DESCRIPTION: SEQ ID NO:11:

```
GAGTTCTTGG TGGCAGAGAG CACG                                              24
```

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "3' mutagenic primer"

-continued (xi) SEQUENCE DESCRIPTION: SEQ ID NO:12:

CGTGCTCTCT GCCACCAAGA AGTC 24

POLYNUCLEOTIDES ENCODING A NOVEL SHC-BINDING PROTEIN

FIELD OF INVENTION

The present invention relates generally to the identification and isolation of a novel Shc-binding proteins, to novel nucleic acid molecules encoding such polypeptides and more particularly to the isolation and identification of a unique Shc binding protein designated PAL (Protein expressed in Activated Lymphocytes), and nucleic acid molecules encoding PAL.

BACKGROUND

The ubiquitously expressed Shc adapter proteins play a role in coupling growth factor receptor activation to intracellular signaling pathways. The mammalian Shc gene encodes at least three overlapping proteins with molecular weights of approximately 46 kDa, 52 kDa and 66 kDa (also called the p46, p52, and p66 isoforms or proteins, Bonfini et al., *TIBS* 21:257–261 (1996); Migliaccio et al., *EMBO J.* 16:706–716 (1997); Pelicci et al., *Cell* 70:93–104 (1992)). All three protein products share a carboxy terminal Src Homology 2 (SH2) domain, a central glycine/proline rich domain with homology to alphal collagen (CH1), and an amino terminal phosphotyrosine binding (PTB) domain which is different from the SH2 domain. The p52 and p46 isoforms differ only by 46 amino acids at the extreme amino terminus and are generated by the use of alternative translation initiation sites (Pelicci et al., *Cell* 70:93–104 (1992)). The p66 isoform is produced via alternative splicing of the Shc gene and contains an amino terminal extension which encodes a second collagen homology region (CH2) in addition to the common PTB, Ch1, and SH2 domains. Interestingly, it has recently been demonstrated that the expression of p66 is more restricted, and that some of its biological properties are distinct from those of the p52 and p46 Shc isoforms (Bonfini et al., *TIBS* 21:257–261 (1996); Migliaccio et al., *EMBO J.* 16:706–716 (1997)).

Shc proteins are typically tyrosine phosphorylated following activation of receptor tyrosine kinases (van der Geer et al, *Ann. Rev. Cell Biol.* 10:251–337 (1994)), such as the epidermal growth factor receptor (EGFR) (Pelicci et al., *Cell* 70:93–104 (1992)), the platelet-derived growth factor receptor (PDGFR) (Yokote et al., *J. Biol. Chem.* 269:15337–15343 (1994)), the nerve growth factor receptor (TrkA) (Obermeier et al., *EMBO J.* 13:1585–1590 (1994)), the insulin receptor (Pronk et al., *J. Biol. Chem.* 268:5748–5753 (1993)), and erbB-2 (Segatta et al., *Oncogene* 9:2105–2112 (1993)), as well as following activation of receptors that lack intrinsic tyrosine kinase activity, such as the T-cell receptor (TCR) (avichandran et al., *Science* 262:902–905 (1993)), the B-cell receptor (Saxton et al., *J. Immunol.* 153:623–636 (1994)), the receptors for the interleukins (Bums et al., *J. Biol. Chem.* 268:17659–17661 (1993); Cutler et al., *J. Biol. Chem.* 268:21463–21465 (1993); Ravichandran et al., *J. Biol. Chem.* 269:1599–1602 (1994)), and the erythropoietin receptor (Damen et al., *Blood* 82:2296–2303 (1993)). Additionally, tyrosine phosphorylation of Shc proteins has been detected after activation of G-protein coupled receptors (Cazaubon et al., *J. Biol. Chem.* 269:24805–24809 (1994); Chen et al., *EMBO J.* 15:1037–1044 (1996);al., Ptazniket et al. *J. Biol. Chem.* 270:19969–19973 (1995); Touhara et al., *Proc. Natl. Acad Sci. USA*. 92:9284–9287 (1995); van Biesen et al., *Nature* 376:781–784 (1995)), ligation of integrins (Maniero et al., *EMBO J..* 14:4470–4481(1995); Wary et al., *Cell* 87:733–743 (1996)), and in cells expressing activated Src, Fps, Sea or Lck (Baldari et al., *Oncogene* 16:1141–1147 (1995); Crowe et al., *Oncogene* 9:537–544 (1994); McGlade et al., *Proc. Natl. Acad. Sci. USA* 89:8869–8873 (1992); Pelicci et al., *Oncogene* 11:899–907 (1995)), which implicates Shc proteins as important substrates of cytoplasmic tyrosine kinases.

Shc Protein Binding

Shc proteins are able to directly bind to tyrosine-phosphorylated peptides or proteins, including activated receptor tyrosine kdnases, typically by virtue of their SH2 or PTB domains (Bonfini et al., *TIBS* 21:257–261 (1996); Pawson, *Nature* 373:573–579 (1995)). The Shc SH2 domain preferentially binds to tyrosine phosphorylated peptides in the sequence context pY-E/I -X-I/L/M (where X represents any amino acid) (Songyang et al., *Mol. Cell. Biol.* 14:2777–2785 (1994)) and mediates the binding of Shc to the PDGFR (Songyang et al., *Mol. Cell. Biol.* 14:2777–2785 (1994)), EGFR (Pelicci et al, *Cell* 70:93–104 (1992)), receptor tyrosine kinase (RET) (Pronk et al. *J. BioL Chem.* 268:5748–5753 (1993)), and the CD3 zeta chain (Ravichandran et al., *Science* 262:902–905 (1993)). The PTB domain of Shc proteins also recognizes tyrosine phosphorylated peptides, but in a different context by selecting specific residues amino terminal to the phosphorylated tyrosine (Songyang et al., *J. Biol Chem.* 270:14863–14866 (1995)). The Shc PTB domain has been shown to bind directly to N-P-X-pY sequence motifs in the cytoplasmic domains of the EGFR (Blaikie et al., *J. Boil Chem.* 269:23031–32034 (1994)), TrkA (Diklic etal.,*J. Biol. Chem.* 270:15125–15129 (1995)), RET (Lorenzo et al., *Oncogene* 14:763–771 (1997)), and the IL-2Rβ chain (Ravichandran et al., *Proc. Natl. Acad. Sci. USA* 28:5275–5280 (1996)).

Phosphorylated Shc proteins are also able to associate with the Grb2 adapter protein by binding of the Grb2 SH2 domain to the phosphorylated tyrosine residue 317 (Y317) within the CH1 domain of Shc proteins (Rozakis-Adcock et al., *Nature* 360:689–692 (1992); Salcini et al., *Oncogene* 9:2827–2836 (1994)). Grb2 is stably associated with the Ras guanine nucleotide exchange factor, SOS (Batzer et al., *Nature* 363:85–88 (1993); Buday et al., *Cell* 73:611–620 (1993); Chardin et al., *Science* 260:1338–1343 (1993); Egan et al., *Nature* 363:45–51 (1993); Rozakis-Adcock et al., *Nature* 363:83–85 (1993)), and membrane localization of the Grb2-SOS complex results in activation of Ras (Aronheim et al., *Cell* 78:949–961 (1994)). Therefore, it has been proposed that Shc proteins are involved in coupling cell surface receptors to Ras activation. Several studies on the effects of Shc protein over expression provide support for this hypothesis. First, co-expression of a dominant negative mutant of Ras blocks neurite outgrowth in PC12 cells induced by Shc protein over expression (Rozakis-Adcock et al., *Nature* 360:689–692 (1992)). Second, over-expression of Shc protein in NIH 3T3 fibroblasts results in transformation (Pelicci et al., *Cell* 70:93–104 (1992)), and this can be abrogated by mutation of the presumed Grb2 binding site (Salcini et al., *Oncogene* 9:2827–2836 (1994)). Also, over-expression of Shc protein enhances EGF induced activation of MAP kinases (Migliaccio et al., *EMBO J.* 16:706–716 (1997)), and cell motility and growth in response to hepatocyte growth factor (HGF) (Pelicci et al., *Oncogene* 10:1631–1638 (1995)).

Shc Protein Ras-independent Binding

The modular structure of Shc proteins permits their interaction with multiple signaling molecules, suggesting that Shc proteins could finction to couple activated receptors to pathways other than Ras. Two additional sites of Shc protein tyrosine phosphorylation have recently been mapped to tyrosine residues 239 and 240 (Y239/240) (Gotoh et al., *EMBO J.* 15:6197–6204 (1996); Harmer et al., *Mol. Cell. Biol.* 17:4087–4095 (1997); van der Geer et al. *Curr. Biol.* 6:1435–1444 (1996)). Tyrosine 239 is present within a Grb-2 SH2 binding motif, and has been demonstrated to associate with Grb-2 in vivo (Gotoh et al., *Mol. Cell. Biol.* 17:1824–1831 (1997); Harmer et al. *Mol. Cell. Biol.* 17:4087–4095 (1997)). The Y239/240 phosphorylation sites may also couple Shc proteins to additional downstream SH2 containing proteins, since phosphopeptides corresponding to Y239/240 have been demonstrated to bind to a variety of as yet, unidentified proteins, in addition to Grb2 (van der Geer et al., *Curr. Biol.* 6:1435–1444 (1996)). A novel role for Shc proteins has been suggested in which phosphorylation of Y239/ Y240 leads to c-myc induction, and suppression of apoptosis in Ba/F3 cells, in a Ras-independent manner (Gotolet al., *EMBO J.* 15:6197–6204 (1996)).

The Shc PTB domain has been demonstrated to bind directly to the cytoplasmic enzyme SHIP, an SH2 domain containing inositol 5-phosphatase, in response to growth factor and cytokine stimulation in hematopoietic cells (Damen et al., *Proc. Natl. Acad Sci. USA* 93:1689–1693 (1996); Kavanaugh et al., *Curr. Biol.* 6:438–445 (1996); Lioubin et al., *Genes & Development* 10:1084–1095 (1996)). Furthermore, proline rich sequences in the Shc CH1 domain are proposed to mediate the interaction between Shc proteins and the SH3 domain of eps8, a tyrosine phosphorylated protein involved in EGF receptor mediated signaling (Bonfini et al., *TIBS* 21:257–261 (1996); Matoskova et al., *Mol. Cell. Biol.* 15:3805–3812 (1995)). Therefore, it is likely that Shc proteins participate in diverse signal transduction pathways by interacting with multiple cytoplasmic signaling molecules. Shc proteins are generally believed to be involved in various cell proliferation pathways. Specifically, Shc proteins appear to be involved in signaling pathways that lead to cell division.

SUMMARY OF THE INVENTION

The invention is directed to an isolated and purified Shc binding protein designated PAL (Protein expressed in Activated Lymphocytes ) and to nucleic acids encoding the proteins.

In certain embodiments, the invention is directed to a PAL polypeptide comprising the polypeptide set out as SEQ ID NO.:2; the polypeptide set out as SEQ ID NO.:4; a polypeptide that is at least 75 percent identical to the foregoing polypeptides; and a biologically active fragment, homolog or variants, conserved variants, allelic variant analogs. The PAL polypeptide optionally may have an amino terminal methionine. The polypeptides of the invention may also be covalently modified with for example water soluble polymers, and fusion with peptides preferably at the amino or carboxy terminus of a PAL polypeptide according to the invention. Also encompassed by the invention are polypeptides having about 50% sequence similarity to the polypeptides set out as SEQ ID NOS.:2 or 4.

The invention is further directed to anti-PAL antibodies directed against such PAL polypeptides.

In certain embodiments, the present invention is directed to a polynucleotide molecule encoding a polypeptide selected from the group comprising of the polynucleotide molecule of SEQ ID NO.:1; the polynucleotide molecule of SEQ ID NO.:3; a polynucleotide molecule encoding the polypeptide of SEQ ID NO.:2 or a biologically active fragment thereof; a polynucleotide molecule that encodes a polypeptide that is at least 75 percent identical to the polypeptide of SEQ ID NO.:2; a polynucleotide molecule encoding the polypeptide of SEQ ID NO.:4 or a biologically active fragment thereof; a polynucleotide molecule that encodes a polypeptide that is at least 75 percent identical to the polypeptide of SEQ ID NO.:4; a polynucleotide molecule that hybridizes under stringent conditions to a polynucleotide molecule complementary to any of items (a)–(f) below; and a polynucleotide molecule that is the complement of any of items (a)–(g) below.

In other embodiments, the invention is directed to vectors comprising these polynucleotide molecules, and host cells, either prokaryotic or eukaryotic, comprising the vectors, and recombinant host cells containing the polynucleotide molecules or vectors according to the invention.

In other embodiments, the invention is directed to a polynucleotide or fragment(s) thereof, which can be used to detect the presence of polynucleotide molecules that encode PAL polypeptides. In other embodiments, the invention provides methods of using such nucleic acids or fragments to detect the presence of nucleic acids encoding PAL polypeptides.

In other embodiments, the invention provides a process for producing a PAL polypeptide including the polypeptides described above.

In yet other embodiments, the invention is directed to a process for producing a recombinant host cell that expresses a PAL polypeptide according to the invention, and to methods of producing PAL polypeptides using those host cells.

In still another embodiment, the invention is directed to a mammalian cell containing a PAL polypeptide encoding DNA and modified in vitro to permit higher expression of PAL polypeptide by means of a homologous recombinational event consistent of inserting an expression regulatory sequence in functional proximity to the PAL encoding DNA thereby increasing the expression of a PAL polypeptide by activating of an endogenous PAL gene.

In other embodiments, the invention provides a process of using such recombinant host cells to screen compounds or compositions for their ability to block cell division or proliferation.

In yet other embodiments, the invention provides a transgenic animal that produces PAL polypeptide, according to the present invention on to transgenic animals in which one or more of its PAL genes is disrupted or "knocked out" and The invention also provides a process of using such a transgenic animal to screen compounds or compositions for their ability to block cell division or proliferation by measuring the effect on PAL production and inhibition of cell proliferation in vivo in the transgenic animal by the compounds or compositions.

BRIEF DESCRIPTION OF THE DRAWINGS

FIG. 1 depicts the nucleic acid sequence of the cDNA encoding human PAL (SEQ ID NO.:1).

FIG. 2 depicts the deduced amino acid sequence for human PAL as translated from the cDNA (SEQ ID NO.:2).

FIG. 3 depicts the nucleic acid sequence of the cDNA encoding murine cDNA (SEQ ID NO.:3)

FIG. 4 depicts the deduced amino acid sequence for murine PAL as translated from the cDNA (SEQ ID NO.:4).

FIG. 5 depicts the amino acid sequence comparison between human PAL SEQ ID NO.:2) and the murine PAL SEQ ID NO.:4) polypeptides.

DETAILED DESCRIPTION OF THE INVENTION

A novel Shc binding protein designated PAL (Proteinexpressed in ActivatedLymphocytes) and nucleic acids encoding the protein are disclosed herein. DNAs encoding mouse PAL (mPAL), and human PAL (hPAL) have been isolated and characterized. Such DNAs may be used to obtain PAL DNAs from other species using methods well known in the art. The term PAL is used generically and is not intended to be species specific.

The predicted amino acid sequence encoded by mPAL DNA contains 23 tyrosine residues, several of which are embedded in consensus binding motifs for SH2 domains. In addition, two highly acidic regions are encoded by the mPAL DNA. Comparison of both the nucleotide and protein sequences of mPAL with the GenBank databases revealed no significant homology between mPAL and any previously identified proteins. We have identified several related expressed sequence tags (ESTs) represent human and rat homologues of mPAL. In addition several short murine and human ESTs with approximately 50% sequence similarity to regions of mPAL were identified, suggesting that additional mPAL related genes exist.

PAL binds specifically to the Shc SH2 domain and, unlike previously described Shc SH2-protein interactions, the association of PAL and Shc protein is phosphotyrosine independent. Both PAL RNA and protein expression are restricted to tissues containing actively dividing cells and to proliferating cells in culture. PAL expression is induced upon growth factor stimulation and is down regulated upon growth inhibition. This pattern and timing of PAL expression and its association with the Shc protein, suggests a role for this protein in signaling pathways governing cell cycle progression.

PAL is also more highly expressed in tumor cell lines than in normally proliferating cell lines, which indicates that PAL, or nucleic acids that encode all or a portion of PAL, may serve as tumor markers for diagnosing cancer or localizing tumor cells. Moreover, the PAL may also be used as a target in test systems, such as transformed cell lines or transgenic animals, to screen for drugs that may be useful for blocking the promotion of cell proliferation, more particularly in screening candidate drugs for cancer treatment.

There are also circumstances where cell division or proliferation are desirable, such as in the stimulation of hematopoiesis following chemotherapy or radiation therapy or to encourage or stimulate growth of cultured mammalian cells. In such settings, PAL may be used therapeutically to stimulate cell proliferation either by the introduction of expressible PAL encoding DNA into cells (gene therapy) or by the use of PAL polypeptides to directly stimulate hematopoiesis either in an in vivo or ex vivo context.

Yet a further aspect of the present invention is to provide nucleic acid molecules encoding PAL polypeptides, and encompassed in the present invention are methods of preparing such nucleic acid molecules and polypeptides.

The present invention also provides methods of detecting or determining the presence of tumor cells using nucleic acids that encode all or a portion of PAL polypeptides or using antibodies directed against PAL polypeptides.

Another aspect of the present invention provides methods of screening compounds or compositions for their ability to block cell division or proliferation using cell lines or transgenic animals that comprise nucleic acids that produce PAL polypeptides. Such cell lines and such transgenic animals are also provided according to certain embodiments of the present invention.

Also included in the scope of this invention are PAL polypeptides such as the polypeptide of SEQ ID NO.:2 and SEQ ID NO.:4 and related biologically active polypeptide fragments, homologs, variants, conserved variants, allelic variants and derivatives thereof Further included within the scope of the present invention are nucleic acid molecules that encode these polypeptides, and methods for preparing the polypeptides.

The invention is also directed to non-human mammals such as mice, rats, other rodents, rabbits, goats, sheep, and other animals including farm animals, in which one or both of copies of the gene encoding the animal's equivalent of human PAL has been disrupted ("knocked out") so as to prevent expression of an active gene product or to significantly reduce the activity of an expressed gene product. Such mammals may be prepared using techniques and methods such as those described in U.S. Pat. No. 5,557,032, incorporated herein by reference.

The present invention further includes non-human mammals such as mice, rats, other rodents, rabbits, goats, sheep, and other farm animals in which the gene (or genes) encoding PAL polypeptides (either the native form of PAL for the mammal or a heterologous PAL gene), is over expressed by the mammal by way of the introduction of expression regulatory sequences in functional proximity to the animal's endogenous PAL gene or by introducing into the animal a transgene comprising an expression regulatory sequence and a PAL encoding DNA, thereby creating a "transgenic" mammal. Such transgenic mammals may be prepared using well known methods such as those described in U.S. Pat. No. 5,489,743 and PCT patent application No. WO94/28122, published Dec. 8, 1994.

The term "PAL protein" or "PAL polypeptide" as used herein refers to any protein or polypeptide having the properties described herein for PAL. The PAL polypeptide may or may not have an amino terminal methionine, which may depend on the manner in which it is prepared. By way of illustration, PAL protein or PAL polypeptide refers to (1) an amino acid sequence encoded by PAL nucleic acid molecules as defined in any of items (a)–(f) below, and peptide or polypeptide fragments derived therefrom, (2) naturally occurring allelic variants of the PAL gene which result in one or more amino acid substitutions, deletions, and/or insertions as compared to the PAL polypeptide of SEQ ID NO.:3 or SEQ ID NO.:4, and/or (3) chemically modified derivatives as well as nucleic acid and or amino acid sequence variants thereof as provided for herein.

As used herein, the term "PAL fragment" refers to a peptide or polypeptide that is less than the full length amino acid sequence of naturally occurring PAL protein but has a biological activity of or similar to PAL polypeptide or PAL protein described above. Such a fragment may be truncated at the amino terminus, and/or the carboxy terminus, and/or internally, and may be chemically modified. Such PAL fragments may or may not include an amino terminal methionine. PAL fragments also include immunologically active fragments of the PAL polypeptide, the fragments capable of eliciting antibody response in a host animal.

As used herein, the term "PAL derivative" or "PAL variant" refers to a PAL polypeptide, protein, or fragment that 1) has been chemically modified, as for example, by addition of one or more polyethylene glycol molecules, sugars, phosphates, polypeptides (i.e. fusion proteins including fusion with immuoglobulin molecules or fragments thereof such as is described in WO97/24440, incorporated herein by reference,), or other such molecules not naturally attached to wild-type PAL polypeptide, the modifications may be covalent modifications, a "PAL variant" that 2) contains one or more nucleic acid or amino acid sequence substitutions, deletions, and/or insertions as compared to the PAL nucleic acid or amino acid sequence set forth in SEQ ID No.:1 or 2. The PAL polypeptide(s) or fragment(s), variant(s) including the variants discussed above or homolog(s) of the PAL polypeptide(s) may be chemically modified, i.e., glycosylated, phosphorylated, and/or linked to a polymer, as described below, they may have an amino terminal methionine, depending on how they are prepared and may also comprise a fusion protein or fusion polypeptide.

The full length PAL polypeptide or fragment thereof can be prepared using well known recombinant DNA technology methods such as those set forth in Sambrook et al. *Molecular Cloning: A Laboratory Manual*, Cold Spring Harbor Laboratory Press, Cold Spring Harbor, N.Y. (1989) and/or Ausubel et al., eds, *Current Protocols in Molecular Biology*, Green Publishers Inc. and Wiley and Sons, N.Y. (1994). A gene or cDNA encoding the PAL protein or fragment thereof may be obtained for example by screening a genomic or cDNA library, or by PCR amplification. Alternatively, a gene encoding the PAL polypeptide or fragment may be prepared by chemical synthesis using methods well known to the skilled artisan such as those described by Engels etal., *Angew. Chem. Intl. Ed.*, 28:716–734 (1989). These methods include, inter alia, the phosphotriester, phosphoramidite, and H-phosphorate methods for nucleic acid synthesis. A preferred method for such chemical synthesis is polymer-supported synthesis using standard phosphoramidite chemistry. Typically, the DNA encoding the PAL polypeptide will be several hundred nucleotides in length. Nucleic acids larger than about 100 nucleotides can be synthesized as several fragments using these methods. The fragments can then be ligated together to form the full length PAL polypeptide. Usually, the DNA fragment encoding the amino terminus of the polypeptide will have an ATG, that encodes a methionine residue. This methionine may or may not be present on the mature form of the PAL polypeptide, depending on whether the polypeptide produced in the host cell is secreted from that cell.

In some cases, it may be desirable to prepare nucleic acid and/or amino acid variants or analogs of naturally occurring PAL. Nucleic acid variants or analogs (wherein one or more nucleotides and/or amino acids are designed to differ from the wild-type or naturally occurring PAL) may be produced using site directed mutagenesis or PCR amplification where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well. For example, in Wayne et al., *EMBO J.* 2:1827–1829 (1983), the authors teach a method for deletion mutagenesis, that was used to generate mutants of the TyrTS gene. Huang et al., *Cell* 48:129–136 (1987), analyzed the functional domains of Pseudomonas exotoxin using a deletion analysis of the gene expressed in *E. coli*. In 1986, Zumstein et al., *J. Mol. Biol.* 191: 333–340, described the analysis of structural and functional domains of *E. coli* DNA Topoisomerase I using insertion and deletion mutagenesis. In DeChiara et al., *Methods in Enzymol.* 119:403–415, the authors describe procedures for in vitro DNA mutagenesis of human leukocytes interferon. Other publications describing mutagenesis of cloned genes and subsequent testing of the polypeptide encoded thereby include Doyle et al., *J. Cell Biol.* 103: 1193–1204 (1986), and others. Preferred nucleic acid variants or analogs are those containing nucleotide substitutions accounting for codon preference in the host cell that is to be used to produce PAL. Other preferred variants or analogs are those encoding conservative amino acid changes as described above (e.g., wherein the charge or polarity of the naturally occurring amino acid side chain is not altered substantially by substitution with a different amino acid), as compared to wild type, analogs of PAL polypeptide(s), and/or those designed to either generate a novel glycosylation and/or phosphorylation site(s) on PAL, or those designed to delete an existing glycosylation and/or phosphorylation site(s) on PAL.

As used herein, the terms "biologically active" when used in the context of any polypeptide(s), fragment(s), derivative(s), homolog(s) and variant(s) refers to a molecule having a biological activity of PAL such as the ability to stimulate cell growth or division if either in vivo or in vitro as well as affecting signaling pathways governing cell cycle progression. According to the present invention the ability to induce antibody production in a suitable host is also within the meaning of "biological activity" and "immunologically active". As used herein, the terms "effective amount" and "therapeutically effective amount" refer to the amount of PAL necessary to support one or more biological activities of PAL as set forth above. The PAL polypeptides that have use in practicing the present invention may be naturally occurring full length polypeptides, or truncated polypeptides or variant homologs or analogs or derivatives or peptide fragments. Illustrative analogs include those in which one or more divergent amino acids between two species are substituted with the divergent amino acid from another species. Divergent amino acids may also be substituted with any other amino acid whether it be a conservative or a non-conservative amino acid. More particularly PAL analogs may comprise the amino acid sequence set out as SEQ ID NOS.:2 or 4, wherein one or more amino acids selected from the group consisting of amino acids 4, 5, 6, 7, 10, 13, 14, 17, 19, 21, 22, 23, 25, 27, 29, 32, 33, 34, 38, 40, 42, 46, 47, 49, 50, 51, 54, 55, 56, 57, 58, 59, 60, 66, 69, 71, 75, 99 103, 104, 116, 125, 130, 132, 136, 137, 148, 149, 150, 151, 153, 154, 159, 160, 161, 162, 171, 172, 182, 186, 187, 189, 191, 203, 241, 288, 292, 321, 324, 326, 327, 331, 332, 340, 341, 348, 349, 352, 354, 356, 357, 358, 361, 364, 369, 372, 377, 378, 384, 395, 429, 431, 439, 443, 450, 452, 477, 478, 484, 499, 503, 532, 535, 553, 559, 560, 562, 563, 564, 565, 570, 571, 573, 574, 575, 577, 580, 582, 583, 588, 589, 590, 592, 593, 594, 598, 599, 601, 602, 604, 605, 608, 609, 615, 619, 621, 623, 627, 628, 645, 652, 653, 655, and 672 is substituted with another amino acid As used herein, the term "PAL" when used to describe a nucleic acid molecule refers to a nucleic acid molecule or fragment thereof that (a) has the nucleotide sequence as set forth in SEQ ID NO.:1 or SEQ ID NO.:3; (b) has a nucleic acid sequence encoding a polypeptide that is at least 75 percent identical, but may be greater than 75 percent, i.e., 85 percent, 95 percent, or even greater than 95 percent identical, to the polypeptide encoded by any of SEQ ID NOS: 2 or 4; (c) is a naturally occurring allelic variant of (a) or (b); (d) is a nucleic acid variant of (a)–(c) produced as provided for herein; (e) has a sequence that is complementary to (a)–(d); and/or (f) hybridizes to any of (a)–(e) under high stringency conditions. The term "high stringency conditions" refers to hybridization and washing under conditions that permit only binding of a nucleic acid molecule such as an oligonucleotide or cDNA molecule probe to highly homologous sequences. Exemplary stringent hybridization conditions are as follows: hybridization at 65° C. in 3×SSC, 20 mm NaPO$_4$, pH 6.8 followed by washing at 55° C.–65° C. and washing 0.015 M NaCl, 0.005 M NaCitrate, and 0.1 percent SDS. It is understood by those of skill in the art that variation in these conditions occurs based on the length and GC nucleotide content of the sequences to be hybridized. Formulas standard in the art are available for determining exact hybridization conditions. See Sambrook et al., supra. For example, another stringent wash solution is 0.2 ×SSC and 0.1 percent SDS used at a temperature of between 50° C.–65° C. Where oligonucleotide probes are used to screen cDNA or genomic libraries, the following stringent washing conditions may be used. One protocol uses 6×SSC with 0.05 percent sodium pyrophosphate at a temperature of 35° C.–62° C., depending on the length of the oligonucleotide probe. For example, 14 base pair probes are washed at 35° C.–40° C., 17 base pair probes are washed at 45° C. –50° C., 20 base pair probes are washed at 52° C.–57° C., and 23 base pair probes are washed at 57° C.–63° C. can be increased 2–3° C. where the background non-specific binding appears high. A second protocol utilizes tetramethylammonium chloride (TMAC) for washing oligonucleotide probes. One stringent washing solution is 3 M TMAC, 50 mm Tris-HCI, pH 8.0, and 0.2 percent SDS. The washing temperature using this solution is a function of the length of the probe. For example, a 17 base pair probe is washed at about 45–50° C. PAL encoding nucleic acids also includes nucleic acid sequences that encode PAL polypeptide or a fragment thereof, by the way of degenerate codons.

Percent sequence identity can be determined by standard methods that are commonly used to compare the similarity in position of the amino acids of two polypeptides. By way of example, using a computer program such as BLAST or FASTA, the two polypeptides for which the percent sequence identity is to be determined are aligned for optimal matching of their respective amino acids (the "matched span", which can include the full length of one or both sequences, or a predetermined portion of one or both sequences). Each computer program provides a "default" opening penalty and a "default" gap penalty, and a scoring matrix such as PAM 250. A standard scoring matrix (see Dayhoff et al., *Atlas of Protein Sequence and Structure*, vol. 5, supp.3 (1978)), can be used in conjunction with the computer program. The percent identity can then be calculated using an algorithm contained in a program such as FASTA as:

$$\frac{\text{Total number of identical matches}}{[\text{length of the longer sequence within the matched span}] + [\text{number of gaps introduced into the longer sequence in order to align the two sequences}]} \times 100$$

Polypeptides that are at least 70 percent identical will typically have one or more amino acid substitutions, deletions, and/or insertions as compared with wild type PAL. Usually, the substitutions will be conservative so as to have little or no effect on the overall net charge, polarity, or hydrophobicity of the protein but optionally may increase the activity of PAL. Exemplary conservative substitutions are set forth in Table I below.

TABLE I

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Other variants of the polypeptide may be prepared by aligning a human PAL polypeptide sequence with a mouse PAL polypeptide sequence (or PAL from other species) and identifying the divergent amino acids (FIG. 5). One or more of the divergent amino acids can then be substituted with the diverging amino acid or with other amino acids. Such variants may therefore be a composite polypeptide comprising amino acid sequences derived PAL polypeptides derived from two or more species.

The PAL gene or cDNA can be inserted into an appropriate expression vector for expression in a host cell. The vector is typically selected to be functional in the particular host cell employed (i.e., the vector is compatible with the host cell machinery such that amplification of the PAL gene and/or expression of the gene can occur). The PAL polypeptide or fragment thereof may be amplified/expressed in prokaryotic, yeast, insect (baculovirus systems), and/or eukaryotic host cells. Selection of the host cell will depend at least in part on whether the PAL polypeptide or fragment thereof is to be glycosylated. If so, yeast, insect, or mammalian host cells are preferable; yeast cells will glycosylate the polypeptide, and insect and mammalian cells can glycosylate and/or phosphorylate the polypeptide as it naturally occurs on the PAL polypeptide (ie., "native" glycosylation and/or phosphorylation).

Typically, the vectors used in any of the host cells will comprise a promoter operatively linked usually to the 5' end of a DNA molecule to be expressed. Vectors also typically comprise other regulatory elements as well such as an enhancer(s), an origin of replication element, a transcriptional termination element, a complete intron sequence containing a donor and acceptor splice site, a signal peptide sequence, a ribosome binding site element, a polyadenylation sequence, a polylinker region for inserting the nucleic acid encoding the polypeptide to be expressed, and a selectable marker element. Each of these elements is discussed below. Optionally, the vector may contain a "tag" sequence, i.e., an oligonucleotide sequence located at the 5' or 3' end of the PAL coding sequence that encodes poly-Histidine (such as hexaHis), or another small sequences which may be immunogenic or which may have other biological properties such as the ability to prolong the half-life of the polypeptide or to target the polypeptide to cells, organelles or ligands. This tag will be expressed along with the protein, and can serve as an affinity tag for purification of the PAL polypeptide from the host cell. Optionally, the tag can subsequently be removed from the purified PAL polypeptide by various means such as using a selected peptidase for example.

The 5' flanking sequence may be homologous (i.e., from the same species and/or strain as the host cell), heterologous (i.e., from a species other than the host cell species or strain), hybrid (i.e., a combination of 5' flanking sequences from more than one source), synthetic, or it may be the native PAL 5' flanking sequence. As such, the source of the 5' flanking sequence may be any unicellular prokaryotic or eukaryotic organism, any vertebrate or invertebrate organism, or any plant, provided that the 5' flanking sequence is functional in, and can be activated by the host cell machinery. The 5' flanking sequence may comprise of a tissue specific promoter which directs the expression of the encoded polypeptide in specific cells of tissues.

The 5' flanking sequences useful in the vectors of this invention may be obtained by any of several methods well known in the art. Typically, 5' flanking sequences useful herein other than the PAL 5' flanking sequence will have been previously identified by mapping and/or by restriction endonuclease digestion and can thus be isolated from the proper tissue source using the appropriate restriction endonucleases. In some cases, the full nucleotide sequence of the 5' flanking sequence may be known. Here, the 5' flanking sequence may be synthesized using the methods described above for nucleic acid synthesis or cloning.

Where all or only a portion of the 5' flanking sequence is known, it may be obtained using PCR and/or by screening a genomic library with suitable oligonucleotide and/or 5' flanking sequence fragments from the same or another species.

Where the 5' flanking sequence is not known, a fragment of DNA containing a 5' flanking sequence may be isolated from a larger piece of DNA that may contain, for example, a coding sequence or even another gene or genes. Isolation may be accomplished by restriction endonuclease digestion using one or more carefully selected enzymes to isolate the proper DNA fragment. After digestion, the desired fragment may be isolated by agarose gel purification, Qiagen® column or other methods known to the skilled artisan. Selection of suitable enzymes to accomplish this purpose are readily determined by one of ordinary skill in the art.

The origin of replication element is typically a part of prokaryotic expression vectors purchased commercially that aids in the amplification of the vector in a host cell. Amplification of the vector to a certain copy number can, in some cases, be important for optimal expression of the PAL polypeptide. If the vector of choice does not contain an origin of replication site, one may be chemically synthesized based on a known sequence, and ligated into the vector.

The transcription termination element is typically located 3' of the end of the PAL polypeptide coding sequence and serves to terminate transcription of the PAL polypeptide. Usually, the transcription termination element in prokaryotic cells is a G-C rich fragment followed by a poly T sequence. While the element is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium or it may encode a protein whose expression may be determined by physical means such as by fluorescence or by color or by histochemical means. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Marker genes controlling expression product are detectable by physical means, and comprise of genes encoding the fluorescent green protein. Preferred selectable markers are the kanamycin resistance gene, the ampicillin resistance gene, and the tetracycline resistance gene.

The ribosome binding element, commonly called the Shine-Dalgarno sequence (prokaryotes), or the Kozak sequence (eukaryotes), is necessary for translation initiation of mRNA. The element is typically located 3' to the promoter and 5' to the coding sequence of the PAL polypeptide to be synthesized. The Shine-Dalgarno sequence is varied but is typically a poly-purine (i.e., having a high A-G content). Many Shine-Dalgarno sequences have been identified, each of which can be readily synthesized using methods set forth above and used in a prokaryotic vector.

In those cases where it is desirable for PAL to be secreted from the host cell, a signal sequence may be used to direct the PAL polypeptide out of the host cell where it is synthesized. Typically, the signal sequence is positioned in the coding region of PAL nucleic acid sequence, or directly at the 5' end of the PAL coding region. Many signal sequences have been identified, and any of them that are functional in the selected host cell may be used in conjunction with the PAL gene. Therefore, the signal sequence may be homologous or heterologous to the PAL nucleotide sequence, and may be homologous or heterologous to the PAL polypeptide sequence. Additionally, the signal sequence may be chemically synthesized using methods set forth above. In most cases, secretion of the polypeptide from the host cell via the presence of a signal peptide will result in the removal of the amino terminal methionine from the polypeptide.

In many cases, transcription of the PAL polypeptide may be increased by the presence of one or more introns on the vector; this is particularly true where PAL is produced in eukaryotic host cells, especially mammalian host cells. The introns used may be naturally occurring within the PAL nucleic acid sequence, especially where the PAL sequence used is a full length genomic sequence or a fragment thereof. Where the intron is not naturally occurring within the PAL DNA sequence (as for most cDNAs), the intron(s) may be obtained from another source. The position of the intron with respect to the 5' flanking sequence and the PAL coding sequence is important, as the intron must be transcribed to be effective. As such, where the PAL nucleic acid sequence is a cDNA sequence, the preferred position for the intron is 3' to the transcription start site, and 5' to the poly-A transcription termination sequence. Preferably for PAL cDNAs, the intron will be located on one side or the other (i.e., 5' or 3') of the PAL coding sequence such that it does not interrupt the coding sequence. Any intron from any source, including any viral, prokaryotic and eukaryotic (plant or animal) organisms, may be used to practice this aspect of the invention, provided that it is compatible with the host cell(s) into which it is inserted. Also included herein are synthetic introns. Optionally, more than one intron may be used in the vector.

Where one or more of the elements set forth above are not already present in the vector to be used, they may be individually obtained and ligated into the vector. Methods used for obtaining each of the elements are well known to the skilled artisan and are comparable to the methods set forth above (i.e., synthesis of the DNA, library screening, and the like).

The final vectors used to practice this invention are typically constructed from a starting vectors such as a commercially available vector. Such vectors may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other), and then ligated into the vector.

One other method for constructing the vector calls for conducting all ligations of the various elements simultaneously in one reaction mixture. Here, many nonsense or nonfunctional vectors will be generated due to improper ligation or insertion of the elements. However, the functional vector may be identified and selected by restriction endonuclease digestion.

Preferred vectors for practicing this invention are those which are compatible with bacterial, insect, and/or mammalian host cells. Such vectors include, inter alia, pCRII (Invitrogen, San Diego, Calif.), pBSII (Stratagene, LaJolla, Calif.), and pETL (BlueBacII; Invitrogen).

After the vector has been constructed and a PAL nucleic acid has been inserted into the proper site of the vector, the completed vector may be inserted into a suitable host cell for amplification and/or PAL polypeptide expression.

Host cells may be prokaryotic host cells (such as $E.\ coli$) or eukaryotic host cells (such as a yeast cell, an insect cell, or a vertebrate cell). The host cell, when cultured under appropriate conditions, can synthesize PAL protein which can subsequently be collected from the culture medium (if the host cell secretes it into the medium), or directly from the host cell producing it (if it is not secreted). After collection, the PAL protein can be purified using methods such as molecular sieve chromatography, affinity chromatography, and the like.

Selection of the host cell will depend in part on whether the PAL protein is to be glycosylated or phosphorylated (in which case eukaryotic host cells are preferred), and the manner in which the host cell is able to "fold" the protein into tertiary structure (e.g. proper orientation of disulfide bridges, etc.) such that biologically active protein is produced. However, where the host cell does not synthesize properly folded biologically active PAL, the PAL may be "folded" after synthesis using appropriate chemical conditions as discussed below. It is also well known in the art that the host cell in which a PAL encoding DNA molecule is expressed will affect the glycosylation pattern of the expressed protein with the result being that the protein expressed in a host cell other than that in which it is normally expressed will have a different (e.g. non-native), glycosylation pattern. However, such polypeptides may still maintain full or partial biological activity.

Suitable cells or cell lines may be of mammalian origin, such as Chinese hamster ovary cells (CHO) or mouse 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, human epitheloid carcinoma cell line, HeLa (ATCC CCL-2), mouse L-929 cells, 3T3 lines derived from Swiss (ATCC CRL-1658), Balb-c or NIH/3T3 mice, BHK (ATCC CRL-10 or CRL-8544), or HaK (ATCC CRL-15), hamster cell lines all of which are available from the American Type Culture Collection, in Rockville, Md.

Similarly useful as host cells suitable for the present invention are bacterial cells. For example, the various strains of $E.\ coli$ (e.g., HB101, DH5α, DH10, and MC1061) are well-known as host cells in the field of biotechnology. Various strains of $B.\ subtilis$, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect SF9 cells may be utilized as host cells in the method of the present invention (Mller et al., *Genetic Engineering* 8: 277–298 (1986)).

Insertion (also referred to as "transformation" or "transfection"), of the vector into the selected host cell may be accomplished using such methods as calcium chloride, electroporation, microinjection, lipofection or the DEAE-dextran method. Alternatively, a desired gene may also be cloned into an appropriate "retroviral" or "adenoviral" vector. The desired gene can then be introduced into a host cell by infection. The method selected will in part be a function of the type of host cell to be used and the result desired. These methods and other suitable methods are well known to the skilled artisan, and are set forth, for example, in Sambrook et al., supra, and in Ausubel et al., supra. In another aspect of the invention, the host cells comprising a PAL gene may be used to insert in operative proximity to the endogenous gene, promoter regulatory sequences which increase the level of expression of the PAL gene. Typically, such promoter insertions are accomplished using homologous recombinations. See, for example, PCT International Publication No. WO 94/12650, PCT International Publication No. WO 92/20808, and PCT International Publication No. 91/09955.

The host cells containing the vector or the insertional promoter regulatory sequences (i.e., transformed or transfected), may be cultured using standard media well known to the skilled artisan. The media will usually contain all nutrients necessary for the growth and survival of the cells. Suitable media for culturing $E.\ coli$ cells are for example, Luria Broth (LB), and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of the transformed cells only is added as a supplement to the media. The compound to be used will be dictated by the selectable marker element present on the plasmid with which the host cell was transformed. For example, where the selectable marker element is kanamycin resistance, the compound added to the culture medium will be kanamycin.

The amount of PAL polypeptide produced in the host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If the PAL polypeptide has been designed to be secreted from the host cells, the majority of polypeptide may be found in the cell culture medium. Polypeptides prepared in this way will typically not possess an amino terminal methionine, as it is removed during secretion from the cell. If however, the PAL polypeptide is not secreted from the host cells, it will be present in the cytoplasm (for eukaryotic, gram positive bacteria, and insect host cells) or in the periplasm(for gram negative bacteria host cells), and may have an amino terminal methionine. Methods for designing vector constructs which result in a recombinant protein lacking a N-terminal methionine are known.

For intracellular PAL protein, the host cells are typically first disrupted mechanically or osmotically to release the cytoplasmic contents into a buffered solution. PAL polypeptide can then be isolated from this solution.

Purification of PAL polypeptide from solution can be accomplished using a variety of techniques. If the polypeptide has been synthesized such that it contains a tag such as hexahistidine (PAL/hexatIs), or other small peptide at either its carboxyl or amino terminus, it may be purified in a one-step process by passing the solution through an affinity column where the column matrix has a high affinity for the tag or for the polypeptide directly (i.e., a monoclonal antibody specifically recognizing PAL). For example, polyHistidine binds with great affinity and specificity to nickel, thus an affinity column of nickel (such as the Qiagen nickel columns) can be used for purification of PAL/polyHis. (See for example, Ausubel et al., eds., *Current Protocols in Molecular Biology*, Section 10.11.8, John Wiley & Sons, New York (1993)).

Where the PAL polypeptide has no tag, and where there are no anti-PAL antibodies available, other well known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of any of the foregoing techniques may be combined to achieve increased purity. Preferred methods for purification include polyHistidine tagging and ion exchange chromatography in combination with preparative isoelectric focusing.

If it is anticipated that the PAL polypeptide will be found primarily in the periplasmic space of the bacteria or the cytoplasm of eukaryotic cells, the contents of the periplasm or cytoplasm, including inclusion bodies (e.g., gram-negative bacteria), if the processed polypeptide has formed such complexes, can be extracted from the host cell using any standard technique known to the skilled artisan. For example, the host cells can be lysed to release the contents of the periplasm by French press, homogenization, and/or sonication. The homogenate can then be centrifuged.

If the PAL polypeptide has formed inclusion bodies in the periplasm, the inclusion bodies can often bind to the inner and/or outer cellular membranes and thus will be found primarily in the pellet material after centrifugation. The pellet material can then be treated with a chaotropic agent such as guanidine or urea to release, break apart, and solubilize the inclusion bodies. The PAL polypeptide in its now soluble form can then be analyzed using gel electrophoresis, immunoprecipitation or the like. If it is desired to isolate the PAL polypeptide, isolation may be accomplished using standard methods such as those herein set forth below and in Marston et al., *Methods in Enzymol.*, 182:264–275 (1990).

If PAL polypeptide inclusion bodies are not formed to a significant degree in the periplasm of the host cell, the PAL polypeptide will be found primarily in the supernatant after centrifugation of the cell homogenate, and the PAL polypeptide can be isolated from the supernatant using methods such as those set forth above and/or below.

In those situations where it is preferable to partially or completely isolate the PAL polypeptide, purification can be accomplished using standard methods well known to the skilled artisan. Such methods include, without limitation, separation by electrophoresis followed by electroelution, various types of chromatography (immunoaffinity, molecular sieve, and/or ion exchange), and/or high pressure liquid chromatography. In some cases, it may be preferable to use more than one of these methods for complete purification.

In addition to preparing and purifying PAL polypeptide using recombinant DNA techniques, the PAL polypeptides, fragments, and/or derivatives thereof may be prepared by chemical synthesis methods (such as solid phase peptide synthesis), using methods known in the art such as those set forth by Merrifield et al., *J. Am. Chem. Soc.*, 85:2149 (1964); Houghten et al, *Proc Natl Acad. Sci. USA*, 82:5132 (1985); and Stewart and Young, *Solid Phase Peptide Synthesis*, Pierce Chem. Co., Rockford, Ill. (1984). Such polypeptides may be synthesized with or without a methionine on the amino terminus. Chemically synthesized PAL polypeptides or fragments may be oxidized using methods set forth in these references to form disulfide bridges. The PAL polypeptides or fragments may be employed as biologically active or immunological substitutes for natural, purified PAL polypeptides in therapeutic and immunological processes.

Chemically modified PAL compositions (i.e., "derivatives"), where the PAL polypeptide is linked to a polymer ("PAL-polymers"), are included within the scope of the present invention. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. Included within the scope of PAL-polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran, cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol), and polyvinyl alcohol.

For the acylation reactions, the polymer(s) selected should have a single reactive ester group. For reductive alkylation, the polymer(s) selected should have a single reactive aldehyde group. The polymer may be of any molecular weight, and may be branched or unbranched. A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy or aryloxy-polyethylene glycol.

Pegylation (i.e. modification by the addition of PEG or a PEG derivative), of PAL may be carried out by any of the pegylation reactions known in the art, as described for example in the following references: *Focus on Growth Factors* 3: 4–10 (1992); EP 0 154 316; and EP 0 401 384. Preferably, the pegylation is carried out via an acylation reaction or an alkylation reaction with a reactive polyethylene glycol molecule (or an analogous reactive water-soluble polymer), as described below.

In general, chemical derivatization may be performed under any suitable conditions used to react a biologically active substance with an activated polymer molecule. Methods for preparing pegylated-PAL will generally comprise the steps of (a) reacting an PAL polypeptide with polyethylene glycol (such as a reactive ester or aldehyde derivative of PEG), under conditions whereby PAL becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of polypegylated product.

Generally, conditions which may be alleviated or modulated by administration of the present polymer/PAL include those described herein for PAL molecules in general. However, the polymer/PAL molecules disclosed herein may have additional activities, enhanced or reduced activities, or other characteristics, as compared to the non-derivatized molecules.

PAL nucleic acid molecules, fragments, and/or derivatives that do not themselves encode polypeptides that are active in activity assays may be useful as hybridization probes in diagnostic assays to test, either qualitatively or quantitatively, for the presence of PAL DNA or RNA in mammalian tissue or bodily fluid samples or to produce immunologically active fragments of the polypeptide.

Assays to Screen for Inhibitors or Activators of PAL

In some situations, it may be desirable to inhibit or significantly decrease the level of PAL activity. For instance, inhibiting or reducing the level of PAL activity may be useful in cancer or tumor therapy. Compounds that inhibit PAL activity could be administered either in an ex vivo manner, or in an in vivo manner by subcutaneous or intravenous (i.v.) injection, or by oral delivery, implantation device, or the like. The assays described below exemplify methods useful for identifying compounds that inhibit PAL activity.

For ease of reading, the following definition is used herein for describing the assays:

"Test molecule(s)" refers to the molecule(s) that is under evaluation as an inhibitor of PAL, typically by virtue of its potential ability to block the interaction of PAL with Shc proteins.

Several types of in vitro assays using purified PAL protein or polypeptide may be conducted to identify those compounds that perturb PAL activity. Such a perturbation may be accomplished by compounds that for example inhibit the interaction of PAL with Shc proteins.

In one such assay, purified PAL protein or a fragment thereof (prepared for example using methods described above), can be immobilized by attachment to the bottom of the wells of a microtiter plate. Radiolabeled Shc protein, as well as the test molecule(s) can then be added either one at a time or simultaneously to the wells. After incubation, the wells can be washed and counted using a scintillation counter for radioactivity to determine the degree of PAL/Shc protein binding in the presence of the test molecule. Typically, the molecule will be tested over a range of concentrations, and a series of control "wells" lacking one or more elements of the test assays are used for accuracy in evaluating the results. A variation of this assay involves attaching the Shc protein to the wells, and adding radiolabeled PAL along with the test molecule to the wells. After incubation and washing, the wells can be counted for radioactivity. Test compounds to decrease the binding of Shc protein to PAL represent one class of inhibitors of PAL activity.

Several means are available to "detectably label" PAL. For example, PAL protein can be radiolabeled using $^{125}$I. Alternatively, a fusion protein of PAL may be used wherein the DNA encoding PAL is fused to the coding sequence of a peptide such as the c-myc epitope. PAL-myc fusion protein can readily be detected with commercially available antibodies directed against myc. The PAL protein may also be modified by fusion with an immunoglobulin or fragment thereof (e.g. $F_c$ fragment), which may be detected for example by well known methods. Other markers or labels include chromogenic or fluorogenic markers.

An alternative to microtiter plate type of binding assays comprises immobilizing either PAL or Shc protein on agarose beads, acrylic beads or other types of such inert substrates. The inert substrate to which the PAL or Shc protein is attached placed in a solution containing the test molecule along with the complementary component (either Shc protein or PAL protein), which has been radiolabeled or fluorescently labeled; after incubation, the inert substrate can be collected by centrifugation, and the amount of binding between PAL and Shc protein can be readily assessed using the methods described above. Alternatively, the inert substrate complex can be immobilized in a column and the test molecule and complementary component passed over the column. Formation of the PAL/Shc protein complex can then be assessed using any of the techniques set forth above, i.e., radiolabeling, antibody binding, or the like.

Another type of in vitro assay that is useful for identifying a molecule to inhibit PAL activity is the Biacore Assay System (Pharmacia, Piscataway, N.J.), using a surface plasmon resonance detector system and following the manufacturer's protocol. This assay essentially involves covalent binding of either PAL or Shc protein to a dextran-coated sensor chip which is located in a detector. The test molecule and the complementary component can then be injected into the chamber containing the sensor chip either simultaneously or sequentially, and the amount of binding of PAL/Shc protein can be assessed based on the change in molecular mass which is physically associated with the dextran-coated side of the of the sensor chip; the change in molecular mass can be measured by the detector system.

In some cases, it may be desirable to evaluate two or more test molecules together for use in decreasing or inhibiting PAL activity. In these cases, the assays set forth above can be readily modified by adding such additional test molecule (s) either simultaneously with, or subsequently to, the first test molecule. The remainder of steps in the assay can be as set forth above.

Additional assays may be used to determine whether test molecules can disrupt PAL/Shc protein interaction in cell lines. For example, as noted above, PAL is more highly expressed in tumor cell lines than in normally proliferating cell lines. According to certain embodiments, one may expose a cell line that highly expresses PAL and expresses Shc protein to test molecules to determine whether PAL/Shc protein binding is reduced, whether the production of PAL in the cell line is reduced, and/or proliferation of the cell line is reduced. One can compare the effects of the test molecule by comparing these factors (effect on PAL/Shc protein binding, production of PAL, and/or proliferation of the cell line), in the test cell line (i.e. the one exposed to the test molecule), to a control cell line that is not exposed to the test molecule.

For determining the effect on PAL/Shc protein binding or PAL production, one can remove proteins from the cell or sample and use methods similar to those above that tag or isolate PAL/Shc protein complexes or PAL. For example, one could use immunoaffinity purification technique, which may or may not include the use of fusion constructs for the PAL and Shc.

Similarly, one can use a transgenic animal that over expresses PAL and expresses Shc protein to determine whether test molecules reduce PAL/Shc protein binding, reduce production of PAL in the transgenic animal, and/or reduce tumor growth in the transgenic animal. Conversely, assays may also be used to screen for activators of PAL activity. Such compounds may be useful in promoting cell growth and division both in vitro and in vivo. A person of ordinary skill in the art would readily recognize that several of the foregoing assays which measure the inhibition of PAL may be readily adapted to measure increases in PAL activity. Activators of PAL gene transcription may readily determined using techniques such as reverse transcriptase-polymerase chain reaction techniques, RNAse protection assays and the like. Increased levels of PAL protein are also readily determined by well known techniques such as immuno-affinity techniques.

Also comprehended by the present invention is the use of PAL gene and/or protein(s) including conserved variants, allelic variants, and analogs in a method of stimulating hematopoietic progenitor cell proliferation either in vivo by direct administration to the patient or ex vivo by first obtaining hematopoietic progenitor cells and treating them in culture before administration to a patient. Such treatment may include combinations of PAL polypeptides with other hematopoietic growth factors including but not limited to stem cell factor (SCF), G-CSF, GM-CSF, EPO, CSF-1, IL-1, IL2. IL-3, IL-4, IL-5, IL-6, IL-7, IL-8, IL-9, IL-10, IL-11, IGF-1, leukemia inhibitory factor (LIF), as well as other cytokines. Such a use isenvisioned in the treatment of a group of hematopoietic stem cell disorders which are characterized by a reduction in functional marrow mass, including stromal and or hematopoietic precursor cells.

The following examples are intended for illustration purposes only, and should not be construed as limiting the scope of the invention in any way.

EXAMPLES

Standard methods for library preparation, DNA cloning, and protein expression are set forth in Sambrook et al., eds. *Molecular Cloning: A Laboratory Manual*, Cold Spring Harbor Laboratory Press, Cold Spring Harbor, N.Y. (1989), and in Ausubel et al., eds., *Current Protocols in Molecular Biology*, Wiley, New York, N.Y. (1995). Standard methods for cell culture are set forth in Jacoby et al., *Methods in Enzymology: Cell Culture*, Academic Press Inc., San Diego, Calif. (1979).

In order to identify binding partners for p52 Shc protein a yeast-two hybrid system was used. When full length p52 Shc protein was used as a "bait", a novel protein designated mPAL was isolated multiple times from both T-cell (3 clones), and 11.5 day mouse embryo libraries (8 clones). Further analysis of the interaction in the two-hybrid system demonstrated that mPAL interacts specifically with Shc. Furthermore, mPAL was shown to interact with the isolated SH2 region of p52 Shc but not with its CH1 or PTB domains. One of the cDNAs isolated from the two hybrid screen, encoding nucleotides 42 through 2130 of mPAL, was used to screen a mouse spleen library (Stratagene, LaJolla, Calif.), in an attempt to obtain 5' and/or 3' cDNA sequences. As this approach failed to yield any additional 5' or 3' cDNA sequences, 5' and 3' RACE (Frohman et al., *Proc. Natl. Acad Sci. USA*. 85: 8998–9002 (1980)) were used to obtain additional mPAL nucleotide sequence.

The combined cDNA clones (designated mPAL), encompass 2246 bp (SEQ ID NO.:3). The 2007 bp open reading frame of mPAL includes nucleotides 12 through 2018. The first in frame methionine (at nucleotide 12), is a good match for the Kozak consensus sequence (Kozak et al., *Annu. Rev. Cell. Biol.* 8:197–225 (1992)), and is used here to designate the initiation codon. Thus the cDNA of mPAL encodes a polypeptide of 668 amino acids with a predicted molecular weight of 75,917 Daltons. A second in-frame methionine occurs 16 amino acids downstream from the first, and also appears to be a good match for the Kozak consensus sequence. The use of this methionine codon as an initiation codon results in a protein of 653 amino acids with a predicted molecular weight of 74,407 Daltons.

Example I

Yeast-two Hybrid Screen

In order to identify binding partners for p52 Shc, a yeast two hybrid assay system was used. The yeast two-hybrid assay is based on the fact that many eukaryotic transcriptional activators are composed of two physically separable, functionally independent domains. The yeast GAL4 transcriptional activator protein, for example, contains a DNA-binding domain (GAL4-DB), and a transcriptional activator domain (GAL4-TA). The GAL4-DB recognizes and binds to a sequence (UAS), in the upstream regions of GAL4-responsive genes, while the GAL4-TA interacts with other components of the transcription machinery needed to initiate transcription. Both domains are required to activate a gene and, normally, the two domains are part of the same protein. However, if the two domains are physically separated (e.g. by way of recombinant DNA technology), and expressed in the same host cell, the GAL4-DB and TA peptides do not directly interact with each other and cannot activate responsive genes. (Ma et al. *Cell* 51:443–446 (1988)).

In a yeast two hybrid system, two different cloning vectors are used to generate separate fusions of these GAL4 domains that potentially interact with each other. The recombinant hybrid proteins (hybrid of GAL4 domain and a potential binding protein,) are co-expressed in yeast and are targeted to the yeast nucleus. If the non-GAL4-portions of the two types of hybrid interact with each other, the GAL4-

DB will be tethered to GAL4-TA. As a result of this interaction, GAL4 transcriptional activator will be functionally reconstituted and will activate transcription of reporter genes having upstream GAL4 binding sites making protein-protein interaction phenotypically detectable. The yeast two-hybrid system has been used either to screen libraries for a gene(s) encoding a novel protein(s) that interacts with a known target protein or to test two known, previously cloned proteins for interaction. (Chien et al., *Proc. Natl. Acad Sci.* 88:9578–9583 (1991), incorporated herein by reference).

To use the yeast two-hybrid system to isolate and identify novel Shc-binding proteins, a full length human p52 Shc DNA (Pellici et al., *Cell* 70:93–104 (1992)), was cloned into the pAS-1 vector to generate a fusion between the target protein, Shc, and the DNA binding domain of GAL4. This created the "bait", GAL4-Shc hybrid fusion protein. The yeast strain, (Y153), (Bai and Elledge, *Methods in Enzymol.* 273:331–347 (1996)) was used for transformation and contained both HIS3 and lacZ reporter genes driven by promoters containing GAL4 binding sites, and was deleted for endogenous GAL4 (Bai et al., *Methods in Enzymol.* 273:331–347 (1996)). Yeast clones, transformed with pAS-1 GAL4-Shc, were screened for expression of the GAL4-Shc fusion protein by Western blot analysis of yeast lysates using either monoclonal or polyclonal anti-Shc antibodies as discussed below in Example VI. The GAL4-Shc expressing clones were assayed for transcriptional activation of HIS3 gene based on their ability to grow on His- media, and were assayed for transcriptional activation of lacZ, by measuring β-gal activity using a calorimetric assay. The yeast expressing GAL4-Shc alone were negative for activation of GAL4 driven promoters by both criteria. In an attempt to screen for molecules that bind to Shc-protein "bait", a plasmid cDNA library from resting murine T-cells was obtained (Staudinger et al. *J. Biol. Chem.* 268: 4608–4611 (1993)). In this library, total cDNA obtained from resting T-cells was fused to the transcription activation domain of GAL4, GAL4-TA. Also, a mouse embryo GAL4-TA fusion library (Clontech, Palo Alto, Calif.), was used to transform yeast carrying GAL4-Shc DB fusion constructs. The cDNA libraries were transfected into yeast carrying the Shc-GAL4 DB fusion constructs and clones were selected on His⁻media supplemented with 20 mM aminotriazole. After 72 hours, nitrocellulose replicas of the transfected colonies were made and assayed for β-galactosidase activity directly by a method well known in the art. Sambrook et al., Supra. From the $6 \times 10^6$ clones screened from the T-cell library, and $3 \times 10^6$ clones screened from the mouse embryo library, forty two positive clones were picked and the cDNAs isolated. The isolated cDNAs were checked for insert size and introduced into a second strain of yeast (Y187)(Bai and Elledge, *Methods in Enzymol.* 273:331–347 (1996)). The purpose of this step is twofold, first the isolated cDNA can be tested for β-gal activity alone, or when mated with yeast carrying either GAL-Shc or GAL4 can be fused to other unrelated proteins. This eliminates any false positives. Matings between Y153 carrying the GAL4-Shc plasmid and Y187 carrying the GAL4-cDNA fusion were assayed for β-gal activity to confirm positive clones. Following this procedure, twenty one clones were eliminated as false positives. Clones were classified as false positives if they were positive for β-gal activity on their own or when mated with Y153 carrying the DNA binding domain alone.

The remaining twenty one clones isolated in this first round of screening, were classified as specifically interacting with Shc based on the following criteria: 1) yeast expressing both the cDNA and Shc hybrid proteins were able to grow on His⁻media and were positive for β-gal activity; 2) the isolated cDNA transformed in Y187 was negative for activation of HIS3 and lacZ when mated to yeast carrying the GAL4 DNA binding domain alone; and 3) when mated with Y153, containing GAL4-Shc, the ability to transactivate both reporter constructs restored, but mating of the cDNA constructs with other GAL4 fusions did not result in activation of transcription.

Screening of a random primed library derived from mouse embryo (day 11.5) (commercially available from Clontech), was also carried out. Use of a random primed library allows the detection of Shc binding proteins which require the amino terminal sequences for binding. Also, by using a library from a different tissue, cDNAs not represented in the T-cell library were detected. Finally, the repeat isolation of related molecules from two different libraries support the legitimacy of the interaction being detected.

One of the clones isolated when full length p52 Shc was used as a bait encoded a novel protein sequence designated mPAL. This clone was isolated multiple times from both T-cell (3 clones) and 11.5 day mouse libraries (8 clones). Further analysis of the interaction in the two-hybrid system demonstrated that this molecule interacts specifically with Shc and not with other non-specific GAL4 fusion proteins.

Example II cDNA Library Screening, Isolation of mPAL cDNA and Identification of a Protein Product Encoded by mPAL cDNA A mouse spleen cDNA library (Stratagene, LaJolla, Calif.), was screened with the mPAL cDNA isolated from the yeast-two hybrid screen described above. The mouse spleen library was plated as per manufacturer's instructions. Bacteriophage plaques were immobilized on nylon filters as described in Sambrook et al., supra. Filters were initially prehybridized for a minimum of 4 hours at 42° C. in a solution of 50% formamide, 4×SSPE, 1% SDS, 0.5% skim milk powder, 10% dextran sulphate and 10 mg/ml sheared salmon sperm DNA. A cDNA probe consisting of 1522 bp AfiIII/PstI fragment of the mPAL cDNA isolated from yeast two-hybrid screen was [$^{32}$P]-radiolabeled by random hexamer priming (Pharmacia). [$^{32}$P]-Radiolabeled probe was added at $10^6$ cpm/ml and the filters further incubated for 16 hours at 42° C. Blots were washed twice for 10 minutes at room temperature in 2×SSC, 0.1% SDS, then twice at 56° C. in 0.1×SSC, 0.1% SDS, and then exposed to film. Single phage plaques containing hybridizing cDNAs were isolated, re-plated and rescreened until homogenous populations of phage were obtained. The cDNAs were excised from Lambda Zap II Vector as per manufacturer's instructions (Stratagene), and sequenced. cDNAs corresponding to nucleotides 42 to 2130 encoding mPAL amino acids 16-668, were subcloned into Bluescript SK⁻- (Stratagene), and utilized for in vitro transcription and translation described in more detail below. The protein product produced is called mPAL met2, and details for its production are provided below.

The remaining 5' and 3' cDNA ends of mPAL were identified using 5' and 3' RACE (Frohman, M. A., *RACE: Rapid Amplification of cDNA Ends*, PCR Protocols: A Guide to Methods and Applications eds. Innis, N. A. et al. Academic Press, Inc. (1990)), of Marathon Ready cDNAs from murine embryo and spleen using the manufacturer's instructions (Clontech, Palo Alto, Calif.). A full length construct encoding mPAL amino acids 1–668 was cloned by PCR from murine embryo Marathon Ready cDNA and cloned directly into pCR2.1 (Invitrogen, LaJolla, Calif.). This construct was sequenced for accuracy and was used for in vitro transcription and translation described in more detail below. The protein product is called mPAL met 1 and details of its production are provided below.

Example III

Preparation of GST-Fusion Proteins

This example discusses the preparation and purification of certain fusion proteins that are used in other examples in this application. The Shc S12 mutant (R397A) was generated by using standard PCR-based site-directed mutagenesis technique converting amino acid Arg397 to Ala397. (Heguchi, R., *Recombinant PCR in PCR Protocols: A Guide to Methods and Applications*, eds. Innis, M. A. et al. pp 177–183, Academic Press (1990)). The mutagenesis primers used were:

5' mutagenic primer: GAG TTC TTG GTG GCA GAG AGC ACG (SEQ ID NO.:11)

3' mutagenic primer: CGT GCT CTC TGC CAC CAA GAA GTC (SEQ ID NO.:12)

The PCR product containing the R397A mutation was cloned using BamHi and EcoRI restriction sites into the GST fusion vector, pGEX-2T (Pharmacia). The PAL cDNA encoding amino acids 11 to 648 was cloned using XhoI restriction sites into the pGEX-4T3 vector (Pharmacia). Additional GST-fusion proteins; Shc PTB (Blaikie et al., *J. Biol. Chem.* 269:23031–32034 (1994)); Shc SH2 (Pelicci et al., *Cell* 70:93–104 (1992)); Grb2 SH2 (Rozakis-Adcock et al., *Nature* 360:689–692 (1992)); Vav SH2 (Margolis et al., *Nature* 356:71–74 (1992)); GAP-N SH2, PLCy-N SH2, PLCy-C SH2 (Anderson et al., *Science* 250:979–982 (1990)); and p85-N SH2, p85-C SH2 (McGlade et al., *Mol. Cell. Biol.* 12:991–997 (1992)) have been previously described. Nck SH2 contains amino acids 281–377 of human Nck (Lehmann et al., *Nucl. Acids. Res.* 18:1048 (1990)), and the GST Shc-CH1 contains amino acids 212–376 of human Shc.

GST-SH2 fusion proteins were prepared as follows: DH5α strain of *Escherichia coli* (*E. coli*), a strain commonly used in the art for plasmid transformation was used for the preparation of GST-SH.2 fusion proteins. Transformation competent DH5α cells were prepared as described in Sambrook et al. supra. Competent cells were transformed with a plasmid, pGEX-2T, carrying the GST-SH2 fusion gene. Following transformation, the cells were plated on an agar medium containing ampiciflin to select for transformants carrying the GST-SH2 fusion gene. Log-phase DH5-α cells carrying the GST-SH2 fusion gene were grown in the presence of 100 μg/ml ampicillin, and induced with 1 mM isopropylthiogalactopyranoside (IPTG), for 3 hours at 37° C. The cells were pelleted by centrifugation, lysed in 1 ml of ice-cold NP-40 lysis buffer (50 mM Hepes, pH 7.25, 150 mM NaCl, 2 mM EDTA, 100 μM $ZnCl_2$, 1% (v/v) Nonidet-P40, (NP40), 100 μM sodium pervanadate, 10% (v/v) glycerol, 10 μg/ml aprotinin, 10 μg/ml leupeptin, and 1 mM Pefa-Bloc (Boehringer-Mannheim, Indianapolis, Ind.), sonicated on ice three times for 30 seconds, and the lysates clarified by centrifugation for at 11,000 rpm, 4° C. The lysates were incubated with glutathione-Sepharose beads (Pharmacia) for 30 minutes at 4° C., the beads were washed several times with NP-40 lysis buffer, and were resuspended in an equal volume of phosphate-buffered saline (PBS) containing 1 mM dithiothreitol (DTT). Each of the above mentioned GST-fusion proteins were isolated essentially in the same manner as described. The purified GST-fusion proteins were qualitatively and quantitatively analyzed by SDS-PAGE followed by Coomassie staining, and comparison with known BSA standards.

Example IV

Transfections

Human p52 Shc in plasmid vector pECE has been previously described (Pelicci et al., *Cell* 70:93–104 (1992)). The mouse p66 Shc cDNA was subdloned into pcDNAl (Invitrogen). The mPAL cDNA encoding amino acids 11 to 648 was excised from pACT-mPAL by digestion with XhoI and subdloned into pcDNA3.1 (Invitrogen). 293T cells in 10 cm culture dishes were transfected with 10 μg of pECE-Shc and/or pcDNA3.1-mPAL expression vectors using Lipofectin (Gibco-BRL) according to the manufacturer's instructions. Cells expressing the transfected Shc and/or mPAL genes were selected and used to assay in vivo association between mPAL and Shc described below (Example X).

Example V

Antibodies

Anti-mPAL antibodies were raised in rabbits against the peptide sequence MVPPRPDLAAEKEP (SEQ ID NO.:5), corresponding to amino acids 16 through 29 in the deduced protein sequence of mPAL. An amino terminal cysteine was added to this peptide sequence to facilitate conjugation to keyhole limpet haemocyanin (KLH). The KLH-mPAL conjugate was used to immunize rabbits. Harlow et al., in Antibodies: A Laboratory Manual, Cold Spring Harbor, U.S.A. (1988).

The same mPAL peptide sequence used for immunization was also coupled to a "Sulfolink" column (Pierce, Rockford, Ill.) through an added amino terminal cysteine, and the column was used for affinity purification of anti-mPAL antibodies according to the protocol supplied by the manufacturer (Pierce). Briefly, 3 ml of whole serum collected from immunized animals was incubated on a "Sulfolink" column at room temperature for 1 hour. Unbound proteins are eluted from the column with 3×5 ml of phosphate buffered saline (PBS). Antibodies specifically bound to the column are eluted using an elution buffer (200 mM glycine, pH 2.5). Antibody elution off the column is monitored using a spectrophotometer at $A_{280}$. The antibodies are dialyzed overnight against PBS and stabilized by the addition of 0.1 mg/ml bovine serum albumin. The purified antibody was used for Western blotting and immunoprecipitation.

Unless otherwise indicated, in examples in this application, crude anti-mPAL antibodies was used at a concentration of 1:500 for Western blot analysis and 20 μl per immunoprecipitation, and affinity purified antibody was used at a final concentration of 1 μg/ml for Western blotting and at 2 μg per immunoprecipitation.

Affinity purified anti-Shc antibodies (Pelicci et al., *Cell* 70:93–104 (1992)), were used at a 1:500 dilution for Western blot analysis and 2 μg per immunoprecipitation. In some experiments, a monoclonal anti-Shc antibody (Transduction Laboratories, Lexington, Ky.), was used at a dilution of 1:250.

The anti-phosphotyrosine antibody RC20H (Transduction Laboratories), was used at a dilution of 1:2500 for Western blot analysis. The antiphosphotyrosine antibody 4G10 (UBI) was used for Western blot analysis at a dilution of 1: 1000, anti-EGFR antibody (Upstate Biotechnology, Lake Placid, N.Y.), was used at a dilution of 1:500 for Western blot analysis, and anti-β-tubulin antibody (Amersham, Arlington heights, Ill.), was used at a concentration of 1 μg/ml for Western blot analysis.

Example VI

Immunoprecipitation and Western Blot Analysis

Studies were undertaken to examine the expression of PAL protein in a variety of cell types. Unless otherwise indicated, the following conditions were used for PAL immunoprecipitation and Western blot analysis. For NIH/3T3, P19, and 293 cells a single 10 cm plate of near confluent cells was used for immunoprecipitation and Western blot analysis. Each 10 cm plate of adherent cells was lysed in 1 ml of NP-40 lysis buffer for 15 minutes at 4° C. Tissue lysates were also homogenized in NP-40 lysis buffer using a polytron homogenizer (Kinematica AG, Littau, Switzerland). Lysates were transferred to a 1.5 ml microtuge tube and centrifuged at 10,000×g (maximum speed), for 10 minutes at 4° C. Once clarified by microcentritugation, the total protein in the lysate was quantified by standard procedures. Sambrook et al., supra; Ausubel et al., supra. Typically, a volume of lysate containing 1 mg of total protein was incubated with 20 μl crude anti-mPAL antiserum or 2 μg affinity purified anti-mnPAL antiserum and 100 μl of 10% Protein A Sepharose (Sigma Chemical Co., St. Louis, Mo.), and the volume increased to 1 ml with NP-40 lysis buffer. Samples were incubated at 4° C. with gentle rotation for 1 hour. Immune complexes were then washed three times in 1 ml NP-40 lysis buffer. Samples were boiled for 5 minutes in 40 μl reducing SDS-Laemmli sample buffer prior to loading onto a 10% polyacrylamide gel and separation by SDS-PAGE. Proteins were electrophoretically transferred to Immobilon-P (PVDF) membrane (Millipore, Bedford, Mass.), and incubated in a blocking solution of 5% skim milk powder in TBST (20 mM Tris-HCl, pH 8.3, 150 mM NaCl, 0.05% Tween 20), for a minimum of 1 hour prior to addition of antibody overnight at 4° C. Membranes were washed three times in TBST and incubated for 1 hour at 4° C. with a 1:3000 dilution of HRP-coupled protein A (Biorad, Hercules, Calif.). Following incubation with secondary antibodies, membranes were washed three times in TBST and developed using ECL (Amersham), using the manufacturer's instructions.

Anti-mPAL antibodies specifically recognized in vitro transcribed and translated mPAL (mPAL met2), both by immunoprecipitation and Western blot analysis.

Anti-mPAL antibodies were also used for immunoprecipitations from the murine embryonic cell line, P19. Western blot analysis detected an immunoprecipitating protein of 75 kDa which migrated with approximately the same mobility as in vitro transcribed and translated mPAL. Immunoprecipitation of in vitro transcribed and translated mPAL as well as mPAL immunoprecipitated from P19 cells was blocked by preincubation of the antibody with 50 μg of immunizing peptide, further demonstrating the specificity of this antiserum.

The 75 kDa band detected by anti-mPAL in P19 immunoprecipitates was resolved into two closely migrating bands by SDS-PAGE. In order to investigate whether the doublet was generated by the use of two initiation codons, the migration of mPAL from P19 lysates was compared to in vitro transcribed and translated proteins from two mPAL cDNA constructs. T7 TNT-coupled reticulocyte lysate systems (Promega, Madison, Wis.), was used to transcribe and translate cDNA constructs encoding full length mPAL amino acids 1–668 (metl) in the vector PCR2.1 (Invitrogen), or amino acids 16–668 (met2), in the vector Bluescript SK[31]- (Stratagene), according to the manufacturer's instructions. TNT mPAL met1 represents the predicted full length mPAL open reading frame and includes the initiating methionines encoded at position 12 and 56 of the mPAL cDNA sequence. TNT mPAL met2 lacks the methionine at position 12 but contains the internal ATG at nucleotide position 56. The doublet observed in P19 immunoprecipitates appears to correspond to two distinct immunoreactive proteins produced from TNT mPAL met 1. The TNT mPAL met2 produced only one band comigrating with the lower band in P19 and TNT met1 immunoprecipitates. This suggests that methionines at positions 1 and 16 may be used both in vitro and in vivo.

However, PAL was not immunoprecipitated from cell lines derived from species other than mouse, suggesting that anti-mPAL antibodies are species specific. In fact, cloning of human PAL (as described below), has confirmed that the amino terminal sequence against which our anti-mPAL antibodies were raised is not well conserved in the human protein sequence.

Example VII

GST-Precipitation Experiments

This example describes conditions used for GST-precipitation experiments that are discussed in more detail below. Cell lysates were prepared from 293T cells transiently-transfected with p52 Shc in pECE, p66 Shc in pcDNA1 and/or mPAL in pcDNA3.1 as described above (Example III).

Cell lysates were incubated with approximately 5 μg of GST-fusion protein coupled to glutathione-Sepharose 4B beads for 2 hours at 4° C. The beads were washed 3 times with NP-40 lysis buffer, resuspended in 25 uL of SDS-sample buffer, the proteins resolved on a 10% SDS-polyacrylamide gel, and transferred to Immobilon-P membrane (Mllipore). Western blot analysis for the detection of Shc proteins was carried out using affinity purified anti-Shc antibody at a 1:500 dilution (usually 0.5–1 μg antibody/mL of blocking solution). Similarly Western blot analysis for mPAL was carried out as described above (see Example VI), using the immunoaffinity purified anti mPAL antibody at a 1:500 dilution (usually 0.5–1 μg/mL blocking solution), detection of immunoreactive bands was carried out as described above. The GST fusion proteins were visualized with Coomasie blue staining.

Competition studies assessing the phosphotyrosine dependence of GST-Shc SH2 and mPAL association were carried out in the presence of 10, 50 and 100 mM O-phospho-L-threonine, O-phospho-L-serine, or O-phospho-L-tyrosine which were added to the cell lysates prior to incubation with immobilized GST-Shc SH2 fusion protein. While O-phospho-L-tyrosine inhibited the association of GST-Shc SH2 and mPAL, O-phospho-L-threonine and O-phospho-L-serine had no effect on the association of GST-Shc SH2 and mPAL.

Example VIII

Phosphatase Treatment of PAL,Shc Complexes

PAL was precipitated from mPAL transfected 293T cells with 5 μg of immobilized GST-Shc SH2, washed twice with NP-40 lysis buffer, twice with potato acid phosphatase (PAP) buffer (40 mM PIPES pH 6.0, 1 mM DTT, 20 mg/ml aprotinin, 20 mg/mi leupeptin), and incubated with either PAP buffer alone or with 1.2 U of PAP (Boehringer-Mannheim, Indianapolis, Ind.), in the presence or absence of phosphatase inhibitors (1 mM sodium orthovanadate, 100 mM sodium pyrophosphate, 20 mM sodium fluoride) at 30° C. for 1 hour, followed by three washes with NP-40 lysis buffer. Samples were resolved by SDS-PAGE and immunoblotted with anti-mPAL antibody prepared as described above. As a control, PAL immunoprecipitates were treated with either PAP buffer or PAP (1.2 U), as described above.

Example IX

Northern Blot Analysis

Northern blots containing 2 μg of poly (A)+mRNA isolated from a variety of murine tissues and embryos were purchased from Clontech.

Where specified, total RNA was prepared from cultured cells using the TRIzol Reagent (Gibco/BRL), as per manufacturers instructions. RNA samples (10 μg/lane), were separated on formaldehyde-agarose gels and transferred onto Genescreen nylon membrane (NEN-Dupont, Boston, Mass.), as described by Sambrook et al., supra.

Blots were probed with a 1522 bp AflIII/PstI fragment of the mPAL cDNA which was radiolabeled by random hexamer priming (Pharmacia). Blots were initially prehybridized for 4 hours at 42° C. in a solution of 50% formamide, 4×SSPE, 1% SDS, 0.5% skim milk powder, 10% dextran sulphate and 10 mg/ml sheared salmon sperm DNA. [$^{32}$P]-Radiolabeled probe was then added at $10^6$ cpm/ml and the blot further incubated for 16 hours at 42° C. Blots were washed twice for 10 minutes at room temperature in 2×SSC, 0.1% SDS, then twice at 65° C. in 0.1×SSC, 0.1% SDS, and then exposed to film. The blots were also probed with radiolabeled β-actin cDNA (Clontech) or radiolabeled Shc cDNA as an indicator of RNA loading.

Example X

In vivo Association Between mPAL and Shc

To determine if mPAL and Shc are associated in vivo, a co-immunoprecipitation assay was performed using the human embryonic kidney cell line (293T) (ATCC CRL-1573), co-transfected with pECE-Shc and pcDNA3.1-mPAL expression vectors described in Example IV above. The transfected cells were lysed, immunoprecipitated with a control, non-specific antibody (rabbit anti-mouse IgG), anti-Shc or anti-mPAL antibodies, followed by immunoblotting with anti-Shc and anti-mPAL antibodies. For this work, the immunoprecipitates were washed three times, and the bound proteins resolved via SDS-PAGE. Following electrophoretic transfer to membrane, immunoblotting was performed with anti-Shc and anti-mPAL antibodies. This interaction can be disrupted through addition of 50 μg of immunizing peptide, which demonstrates the specificity of this antibody. Typically 2 μg of affinity purified anti-mPAL antibody was used for immunoprecipitation.

Neither Shc nor mPAL were nonspecifically immunoprecipitated by the control antibody. The characteristic doublet indicative of p52 and p46 Shc was present in the mPAL immunoprecipitate, and likewise, a 75 kDa protein corresponding to mPAL was detected in the Shc immunoprecipitate, indicating that Shc and mPAL associate in vivo. The presence of mPAL immunizing peptide prevented the immunoprecipitation of mPAL, and consequently, Shc was no longer observed to co-immunoprecipitate. The p66 isoform of Shc was also observed to co-immunoprecipitate with mPAL, indicating that the Shc-mnPAL interaction is not limited to the p46 and p52 Shc isoforms.

Example XI

The SH2 Domain of Shc Specifically Associates with mPAL

To determine which domain of Shc associated with mPAL in vitro, precipitation experiments were performed in which immobilized GST and GST-fusion proteins corresponding to the PTB, CH1 or SH2 domain of Shc were incubated with lysate from pcDNA3.1-mPAL-transfected 293T cells, and then subjected to immunoblotting with anti-PAL antibody. These fusion proteins are discussed in Example III, and these antibodies are discussed above in Example V. The conditions used are discussed in Example VII. Only the GST-SH2 domain of She (GST-Shc SH2), precipitated mPAL, indicating that this domain was involved in mediating the association of Shc with mPAL, in agreement with the data obtained in the yeast-two hybrid system.

To examine the specificity of the mPAL-Shc SH2 interaction, a series of GST-SH2 fusion proteins generated from several signal transduction molecules were tested for their ability to precipitate mPAL. A panel of GST-SH2 fusion proteins generated from several signal transduction molecules (Shc PTB domain, Blailde et al., *J. Boil Chem.* 269:23031–32034(1994), Shc SH2 domain, Pellici et al., *Cell* 70:93–104 (1992), Grb2 SH2 domain Rozakis-Adcock et al., *Nature* 360:689–692 (1992), Vav SH2 domain Margolis et al., *Nature* 356: 71–74 (1992), N-terminal SH2 domain of ras-GAP, N-terminal SH2 domain (p85-N) and C-terminal SH2 domain (p85-C) of p85 subunit of PI-3 kinase, N-terminal SH2 domain (PLCγ-N), and C-terminal SH2 domain (PLCγ-C) of phospholipase C-γl Anderson et al., *Science* 250:979–982 (1992), Ellis et al., *Mol. Cell. Biol.* 12:991–997(1992), and Nck SH2 domain, Lehman et al., *Nucl. Acids Res.* 18:1048 (1990), were immobilized on glutathione-Sepharose beads. 5 μg of immobilized GST or GST-fusion protein were individually incubated with 293T-mPAL lysate, the beads washed several times, and the remaining bound proteins resolved via SDS-PAGE, transferred to PVDF membrane, and immunoblotted with anti-mPAL antibody. None of the other tested GST-SH2 domains were found to bind to mPAL, indicating that association of the Shc SH2 domain with mPAL was specific.

Example XII

Interaction of mPAL with the Shc SH2 Domain is not Dependent on Phosphorylation of mPAL In the previous experiments, mPAL precipitated by the Shc SH2 domain was not detected by immunoblotting with anti-phosphotyrosine (anti-pY), antibodies, suggesting that tyrosine phosphorylation of mPAL is not critical for Shc SH2 binding.(results not shown) Additionally, the interaction observed between mPAL and Shc in the yeast-two hybrid system strongly suggests that this interaction is independent of tyrosine-phosphorylation (see Example 1). Furthermore, by virtue of its production in *E. coli.*, recombinant GST-mPAL is not tyrosine-phosphorylated and is yet able to precipitate Shc from NIH 3T3 lysate, supporting the view that tyrosine-phosphorylation of mPAL is not important in the mPAL-Shc SH2 interaction. For this work, 10 μg of immobilized recombinant GST, GST-Shc SH2 domain and GST-mPAL fusion protein were individually incubated with approximately 1 mg of NIH-3T3 cell lysate. The beads were washed several times, and the remaining bound proteins resolved via SDS-PAGE, transferred to PVDF membrane, and immunoblotted with either anti-Shc or anti-mPAL antibodies.

Serine/threonine-phosphorylation-dependent SH2 binding has been reported (Migliaccio et al., *EMBO J.* 16:706–716 (1997); Malek et al., *J. Biol. Chem.* 269:33009–33020(1994); Pendergast et al., *Cell* 66:161–171 (1991)), and thus it was of interest to determine if the mPAL-Shc SH2 interaction was phosphorylation-dependent. To investigate this, GST-Shc SH2 was assayed for its ability to associate with dephosphorylated mPAL. Details for this procedure are provided in Example VIII. mPAL was precipitated from transfected 293T cells with immobilized GST-Shc SH2, treated with potato-acid phosphatase buffer or potato-acid phosphatase (PAP) to dephosphorylate serine, threonine and tyrosine-phosphorylated residues. PAP-treatment of the mPAL immunoprecipitate resulted in a downwards mobility-shift, likely representative of dephosphorylated mPAL. GST-Shc SH2 was able to precipitate dephosphorylated mPAL, supporting the conclusion that the phosphorylation of mPAL is not critical for the mPAL-Shc SH2 interaction.

Free phosphotyrosine competed for binding of mPAL to the Shc SH2 domain, whereas free phosphoserine or phosphothreonine did not, implying that excess free phosphotyrosine, which is able to occupy the phosphotyrosine-binding pocket of the Shc SH2 domain, prevented interaction with mPAL. For this work, 2.5 μg of immobilized GST-Shc SH2 domain fusion protein was incubated with 293T-mPAL lysate in the presence of increasing concentrations of free phosphotyrosine, phosphoserine or phosphothreonine (10, 50, and 100 mM). The beads were washed several times, and the remaining bound proteins resolved via SDS-PAGE, transferred to PVDF membrane, and immunoblotted with anti-mPAL antibody.

To demonstrate that an arginine-to-alanine mutation in the conserved FLVRES, (SEQ ID NO.:6), motif (R397A) in the βB region of the Shc SH2 domain, which disrupts its interaction with phosphorylated EGF receptors, also abrogated binding to mPAL, a Shc SH2 domain mutant (SH2 R 397A)), which is unable to bind to phosphotyrosine-containing substrates (Arg397 mutated to Ala), was generated. The Shc2 (R297A) mutein protein and the wildtype Shc SH2 domain (SH2), were expressed as GST-fusion proteins, and immobilized onto glutathione-Sepharose beads (see Example III above). 5 μg of GST or GST-fusion protein were individually incubated with 293T-mPAL lysate, the beads washed several times, and the remaining bound proteins resolved via SDS-PAGE, transferred to PVDF membrane, and immunoblotted with anti-mPAL antibody. These studies showed that the Shc SH2 mutant protein R397A not only prevented the binding of the mutant protein to phosphorylated EGF receptors, but also abrogated the binding of the Shc SH2 mutant protein to mPAL. This suggests that the mPAL-Shc SH2 interaction may involve structural elements similar to those involved in SH2 phosphotyrosine-peptide interactions.

The mechanism of SH2 binding is novel. Unlike other SH2 domain-phosphopeptide interactions, the mPAL-Shc SH2 interaction appears to be independent of phosphorylation. However, certain structural elements involved in Shc SH2-phosphotyrosine peptide interactions are likely involved in the mPAL-Shc SH2 domain interaction, since occupancy of the phosphotyrosine-binding pocket with free phosphotyrosine, or mutation of the conserved R397 residue involved in phosphotyrosine binding disrupts the mPAL-Shc SH2 domain interaction. It is possible that binding of mPAL to the Shc SH2 domain is mediated by the acidic regions in mPAL because phosphotyrosine independent interactions between SH2 domains of other proteins such as BCR-ABL, Lck and Blk and sequences rich in serine and glutamic acid rich have been previously reported (Joung et al., *Proc. Natl. Acad Sci. USA* 93:5991–5995 (1996); Malek et al., *J. Biol. Chem.* 269:33009–33020 (1994); Pendergast et al., *Cell* 66:161–171 (1991)). In some cases, serine phosphorylation has been shown to be important for binding (Malek et al. *J. Biol. Chem.* 269:33009–33020 (1994); Pendergast et al., *Cell* 66:161–171 (1991)). This does not appear to be the case for the mPAL-Shc protein interaction since phosphatase treatment of mPAL does not abrogate binding, nor is the interaction competed by free phosphoserine or phosphothreonine. The exact nature of the Shc SH2-binding site of mPAL is yet to be elucidated.

Example XIII

Expression of mPAL Correlates with Cellular Proliferation

In order to assess whether expression of mPAL correlates with cellular proliferation and/or development multiple tissue Northern blots of poly A+ RNA extracted from adult murine tissues were purchased from Clontech. A $[^{32}P]$-labeled 1.5 kb AflIII/PstI fragment of mPAL cDNA was utilized as probe. Molecular weight standards were indicated on the membrane. The membrane was exposed to X-ray film overnight at −80° C. Equal loading of mRNA was confirmed by reprobing the membrane with $[^{32}P]$-labeled β-actin cDNA probe.

Northern blot analysis of the multiple tissue RNA blot revealed a single mPAL RNA transcript of less than 2.4 kb in size, in close agreement with the cDNA size of 2.2 kb. mPAL RNA was strongly expressed in the testis, but was present at a much lower level in spleen, lung and heart. mPAL RNA was, however, absent from brain, liver, and skeletal muscle. In developing embryos mPAL RNA expression was detected at all stages of embryonic development. This pattern of expression suggested that mPAL expression is restricted to tissues containing a proliferating cell population, but is absent from quiescent tissues. The low levels of mPAL RNA detected in murine lung and heart may result from tissue contamination with activated lymphocytes, which we have demonstrated, express high levels of mPAL.

In agreement with data obtained by Northern blot analysis, mPAL protein was expressed in mouse spleen, testis and thymus, all of which contain proliferating cells, but was absent from normal quiescent tissues. A wide variety of murine tissues were homogenized in NP40 lysis buffer including brain, heart, kidney, liver, lung, skeletal muscle, pancreas, spleen, testis, thymus, and lymphocytes. Immunoprecipitations of mPAL was performed on 1 mg of total protein from each of these tissues using the same techniques as described for cell lines (Example VI). mPAL protein was expressed in mouse spleen, testis, and thymus, each of which represents a tissue containing actively dividing cells. mPAL was not detectable in other adult tissues which do not normally proliferate in vivo. In addition, it was determined that mPAL protein levels are elevated in all murine cell lines tested to date, provided that the cells are actively proliferating.

A human tumor cell line Northern blot (purchased from Clonetech), was probed with murine PAL cDNA as previously described (Example IX). The Northern blot contained poly (A)+ RNA from the following cell lines: HL-60 (promyelocytic leukemia) (ATCC CCL-240), HeLa Cell S3 (cervical carcinoma) (ATCC CCL-2.2), K562 (chronic myelogenous leukemia) (ATCC CCL-243), MOLT-4 (acute lymphoblastic leukemia) (ATCC CRL-1552), Raji (Burkitt's lymphoma) (ATCC CCL-86), SW480 (colorectal carcinoma) (ATCC CCL-228), A549 (lung carcinoma) (ATCC CCL-185) and G361 (malignant melanoma) (ATCC CRL-1424). Elevated levels of human PAL RNA were detected in all the tumor cell lines. mPAL protein and mRNA were also elevated in tissues containing proliferating cells and in proliferating cell lines, but were absent in normal, quiescent tissues and growth-arrested cells. Factors which stimulate cell cycle progression and proliferation also stimulate mPAL expression, whereas factors which inhibit cellular proliferation, including serum withdrawal, contact inhibition, and terminal differentiation, inhibit the expression of mPAL. Within 24 hours following transfer to a culture medium containing low concentrations of serum (DMEM containing 0.5% fetal bovine serum), NIH(3T3 cells are depleted of both mPAL mRNA (as detected by northern blot analysis), and protein (as detected by immunoprecipitation and Western blot analysis). Cells plated at subconfluent levels express both mPAL protein and RNA. However, within 24 hours of reaching confluence, cells are depleted of mPAL protein and RNA (see Example XV below). At this stage the cells have become post-mitotic.

These data support a role for mPAL in cell proliferation. mPAL may be involved in progression through the cell cycle rather than the immediate early response because mPAL mRNA is expressed during entry into S phase and passage through G2/M. Preliminary data from cyclohexamide treated cells also suggests that mPAL is not an immediate early response gene. Proteins whose expression can be induced by growth factors in the absence of any de novo protein synthesis are considered to be encoded by early response genes. Resting cells (cells in G0), will express early response genes typically within one hour (often within minutes), following stimulation by growth factors. Many early response genes encode transcription factors required for induction of delayed response genes.

To test if a gene is an immediate early response gene, cells are stimulated in the presence of an inhibitor of protein synthesis, such as cyclohexamide. If the mRNA for the protein is detectable, even in the absence of protein synthesis, then this protein is encoded by an early response gene.

Because mPAL RNA and protein are not detected until cells entering S phase (12–16 hours following stimulation by growth factor), it is also unlikely that mPAL is not an early response gene.

Overall, the pattern of expression of mPAL protein and RNA support a role for mPAL in signaling pathways governing cellular proliferation.

Example XIV

Induction of mPAL by Addition of Exogenous Growth Factors

For the examples discussed below, unless otherwise indicted, NIH 3T3, P19, and 293T cells were cultured in Dulbecco's Modified Eagle medium (DMEM) supplemented with 10% fetal bovine serum (Sigma), 200 mM L-glutamine, $5 \times 10^{-5}$ M β-mercaptoethanol, 5 U/ml penicillin C, and 5 µg/ml streptomycin sulfate.

In order to characterize the serum mediated induction of mPAL, NIH 3T3 cells were grown to 70–80% confluence, washed twice in phosphate buffered saline (PBS) and then transferred to media containing 0.5% fetal bovine serum for 48 hours to achieve quiescence. Serum starved cells were then transferred to media containing 20% fetal bovine serum. Samples were harvested for mPAL protein or mPAL RNA isolation at time periods of 0, 1, 4, 8, 12, and 24 hours. Cells isolated at each time point were stained with propidium iodide and subjected to cell cycle analysis by flow cytometry. (Jacoby et al., eds., supra).

In total RNA isolated from serum starved NIH/3T3, mPAL RNA was detectable at low levels 1 hour following stimulation. Levels remained low for 8 hours following addition of serum. Expression, however, increased detectably by 12 hours through 24 hours where RNA levels were high. Detectable protein expression appeared to lag behind RNA levels, as mPAL protein is only detectable at the 24 hour time point. For this work, at each time point, one plate of NI3T3 was NP40 lysed. The mPAL protein was immunoprecipitated from 1 mg of cell lysate as described above. Immunoprecipitated proteins were separated by SDS-PAGE, transferred to Immobilon membrane and immunoblotted with anti-mPAL antibodies. Control immunoprecipitates were prepared from equal amounts of protein. In addition, 10 µg of whole cell lysate was also immunoblotted for Shc.

Cell cycle analysis demonstrated a well synchronized passage of these cells through the cell cycle following addition of fetal calf serum. Cells remained primarily in G0/G1 through 8 hours of stimulation, entered S-phase by 12 hours, and 20% of the cells were in G2M at 24 hours following addition of fetal calf serum. Taken together, these data indicate that mPAL is low or absent in cells in G0/G1, but is elevated in cells committed to cell cycle progression, or actively cycling cells.

Example XV

Expression of mPAL is Down-regulated in Cell Lines by Contact Inhibition and Terminal Differentiation Since mPAL mRNA and protein levels appeared to correlate with cell proliferation in tissues, levels of mRNA were analyzed in proliferating versus contact inhibited NIH3T3 cells in culture. NIH/3T3 cells were plated at approximately 50% confluence in DMEM supplemented with 10% fetal bovine serum, and allowed to proliferate over several days. Levels of mPAL mRNA were measured by Northern blot analysis and evaluated relative to cell confluence. For this work, NIH3T3 cells were plated at a density of approximately 50% confluence. The mRNA was harvested from these cells over five consecutive days, and the percentage confluence of each plate was noted at the time of harvest. The mRNA samples (10 µg/lane), were separated on formaldehyde-agarose gels and transferred onto Genescreen nylon membrane. Blots were probed for mPAL mRNA as described above. This blot was exposed to X ray film at −80° C. for 2 days. Equal loading of mnRNA was confirmed by reprobing the membrane for Shc which remains constant upon contact inhibition. Actively growing, subconfluent NIH3T3 cells expressed relatively high levels of mPAL mRNA. However, within 24 hours following cultures reaching confluence, levels of mPAL mRNA decreased to undetectable levels. In contrast, Shc mRNA levels remained constant throughout the time course, irrespective of cell density.

Levels of mPAL were also measured in the embryonic carcinoma cell line P19 in response to differentiation inducing agents. The embryonic carcinoma cell line, P19, can be induced to differentiate to a neural phenotype by incubation in the presence of retinoic acid, and to a muscle phenotype in the presence of DMSO (McBurney, Int. J. Dev. Biol. 37:35–140 (1993)). Following 6 to 7 days of treatment with retinoic acid, as many as 85% of P19 cells expressed neuronal markers and become post-mitotic (McBurney et al., J. Neurosci. 8:1063–1073 (1988); McBumey, Int. J. Dev. Biol. 37:35–140 (1993)). Additionally, DMSO treated P19 cells differentiated towards mesodermal and endodermal lineages. Approximately 25% cardiac muscle cells are observed following 6–7 days of DMSO treatment (McBurney, Int. J. Dev. Biol. 37:35–140 (1993); Rudnicki et al. J. Cell Physio. 142:89–98 (1990)), while the remainder of cells in culture continue to grow and differentiate into skeletal muscle as well as in to other less well defined cell types (McBurney et al., Int. J. Dev. Biol. 37:35–140 (1993)).

Levels of mPAL protein were measured by immunoprecipitation and Western blot analysis in P19 cells induced to differentiate in the presence of retinoic acid or DMSO. For this work, the pluripotent murine embryonic carcinoma cell line, P19, was induced to differentiate into a neuronal/glial phenotype and into muscle-like phenotype in the presence of retinoic acid and DMSO, as discussed above. The mPAL protein was immunoprecipitated from 1 mg of NP-40 cell lysate from each sample. Immunoprecipitates were separated by SDS-PAGE, transferred to Immobilon and immunoblotted with anti-mPAL. In control experiments, 25 μg of whole cell lysate was subjected to SDS-PAGE and Western blot analysis with 0.5 μg anti-β tubulin antibody/mL of blotting solution as probe to control for equal loading. While the parental, rapidly proliferating P19 cells expressed mPAL protein, DMSO differentiated P19 cells expressed significantly lower levels of mPAL. Furthermore, in P19 cells treated for 7 days in the presence of retinoic acid, mPAL is virtually undetectable. Levels of β-tubulin remain constant throughout differentiation. These data further support the hypothesis that mPAL expression is restricted to proliferating cells and is down regulated upon growth inhibition.

Example XVI

T-cell Activation Results in mPAL

Expression and Formation of a mPAL-Shc Complex

The restricted expression pattern of mPAL suggested that the association of Shc and mPAL in vivo might be limited to specific cell types or to cells which have been induced to proliferate and therefore express high levels of mPAL protein. Since the proliferation rate of primary T cells is readily regulated in vitro, the levels of mPAL expression and its association with Shc were investigated in resting versus activated T cells. Primary murine T cells were isolated from wild type and CTLA4 deficient mice (Walterhouse et al., Science 270:985–988 (1995); Marengere et al., Science 272:1170–1173 (1996)). Wild type murine T cells were activated by cross-linking the T cell receptor on anti-CD3 coated tissue culture plates essentially as described in Marengere et al., J. Immunol. 159:70–76 (1997).

Primary mouse lymphocytes, activated by cross linking CD3, expressed high levels of mPAL, while unstimulated cells did not. For this work, T-cells isolated from wild type mice were stimulated by cross-linking the T-cell receptor with anti-CD3 antibodies. Samples were collected over 4 days and lysed in NP40 lysis buffer. The mPAL protein was immunoprecipitated from 1 mg of lysate from each sample, and the immunoprecipitates were resolved via SDS-PAGE. Following electrophoretic transfer to PVDF membrane, immunoblotting was performed with anti-mPAL antibodies. The blot was then stripped and immunoblotted with anti-Shc antibodies. The timing of the expression of mPAL was coincident with T-cell activation and proliferation. Shc immunoblots of anti-mPAL immunoprecipitates revealed the coprecipitation of Shc with mPAL following T cell activation and concurrent with mPAL expression. Furthermore, constitutively activated primary T-cells isolated from a CTLA4 deficient mouse (Marengere et al., Science 272:1170–1173 (1996); Waterhouse et al., Science 270:985–988 (1995)), expressed mPAL protein which coprecipitated with Shc, while mPAL was undetectable in T cells isolated from a wild type mouse.

Example XVII

Cloning of Human PAL (hPAL)

A. LIBRARY SCREEN

A $[^{32}P]$-labeled 1.5 kb AflIII/PstI fragment of mouse PAL (mPAL) cDNA was used to probe a human HeLa 5'-STRETCH cDNA Library which was purchased from Clontech. The cDNA fragment was separated by 1% agarose gel electrophoresis (as described in Sambrook et al., Supra). The AflIII/PstI fragment was excised from the gel and the cDNA isolated using Qiaex II gel Extraction Kit (Qiagen). 50 ng of the cDNA fragment was labeled with $^{32}p$ by random hexamer priming using the Pharmacia T7 QuickPrime Kit (Pharmacia). Filters were initially prehybridized for 4 hours at 42° C. in a solution of 50% formamide, 4×SSPE, 1% SDS, 0.5% skim milk powder, 10% dextran sulphate and 1 mg/mL sheared salmon sperm DNA. $[^{32}P]$-Radiolabeled probed was then added at 1×10$^6$ CPM/ml and the blot further incubated for 16 hours at 42° C. Filters were washed twice for 10 minutes at room temperature in 2×SSC, 0.1% SDS, then twice for 20 minutes at 56° C. in 0.1×SSC, 0.1% SDS, then exposed to film.

The cDNA sequence of largest of the clones (clone 7.1.1), isolated from the HeLa library screen was utilized to design primers for 5' and 3' RACE in order to obtain the full length cDNA sequence for hPAL from Marathon Ready HeLa cDNA (Clontech).

B. 5' and 3' RACE Conditions

5' and 3' RACE was carried out as a two reaction process using two sets of primers. (Frohman et al., supra).

1. 5' RACE Primers:

Outer primer:
5'-CCTCAGGGACCTTGCAGTCAGCTA-3' (SEQ ID NO.:7)

Nested primer:
5'-CTTTCTCCAGAGACGCCAGCTCCT-3' (SEQ ID No.:8)

2. 3' RACE Primers

Outer primer:
5'-GACTACGCTGGAAAACTGTGTGCT-3' (SEQ ID NO.:9)

Nested primer:
5'-ATGGGATCCATCACTGCAAGGAAG-3' (SEQ ID NO.:10)

3. RACE Reaction Mixture:

"Expand High Fidelity PCR System" (Boehringer Mannheim, Indianapolis, Ind.) polymerase and 10× reaction buffer was used for PCR reactions.

| Primary PCR reaction (50 ul final volume) | |
|---|---|
| Marathon ready cDNA | 5 ul |
| AP1 primer (10 uM) | 1 ul |
| Outer primer (10 uM) | 1 ul |
| dNTP (2.5 mM) | 4 ul |
| 10X PCR buffer | 5 ul |
| Taq polymerase | 0.75 ul |
| dH2O | 33 ul |
| Secondary PCR reaction (50 µl final volume) | |
| 1/50 dilution of Primary reaction | 5 µl |
| AP2 primer (10 uM) | 1 µl |
| nested primer (10 uM) | 1 µl |
| dNTP (2.5 mM) | 4 µl |
| 10X PCR buffer | 5 µl |
| Taq polymerase | 0.75 µl |
| dH2O | 33 µl |

PCR Program:
1. 3 minutes at 94° C.
2. 1 minute at 94° C.
3. 1.5 minutes at 56° C.
4. 3 minutes at 72° C.
5. Return to step 2 for 29 cycles
6. 10 minutes at 72° C.
7. Indefinitely at 4° C. (end of program)

PCR products were gel purified and cloned into pCR2.1 using the TA cloning system purchased from Invitrogen. The full length human cDNA was constructed, using conventional cloning techniques, as a composite from sequences obtained from 3' and 5' RACE and the cDNA clone 7.1.1 originally isolated from the HeLa cDNA library, The full length clone was subsequently subcloned into pBluescript cloning vector (Stratagene).

The foregoing examples are presented by way of illustration and are not intended to limit the invention as set out in the appended claims.

What is claimed is:

1. An isolated polynucleotide encoding a PAL polypeptide that specifically binds the SH2 domain of Shc, wherein said PAL polypeptide comprises the amino acid sequence set out in SEQ ID NO.:2 or SEQ ID NO.:4, identity to SEQ ID NO.:2 or SEQ ID NO.: 4 over the entire length of SEQ ID NO.:2 or SEQ ID NO.:4.

2. The isolated polynucleotide according to claim 1 wherein said polynucleotide is selected from the group consisting of cDNA, genomic DNA, and chemically synthesized DNA.

3. An isolated polynucleotide encoding a PAL polypeptide the polynucleotide being selected from the group consisting of:

(a) the polynucleotide set out as SEQ ID NO.:1 or the polynucleotide set out as SEQ ID NO.:3; and (b) polynucleotides which hybridize under high stringency conditions to the polynucleotides a polynucleotide encoding a PAL polypeptide that specifically binds the SH2 domain of Shc, wherein said PAL polypeptide comprises the amino acid sequence set out in SEQ ID NO.:2 or SEQ ID NO.:4, or an amino acid sequence having greater than 85% identity to SEQ ID NO.:2 or SEQ ID NO.: 4 over the entire length of SEQ ID NO.:2 or SEQ ID NO.:4.

4. A cloning vector which comprises a polynucleotide according to claims 1, 2, or 3.

5. A unicellular host transformed with a polynucleotide according to claims 1, 2, or 3.

6. A method for producing a PAL polypeptide, the method comprising the steps of:

(a) culturing a unicellular host according to claim 5 under suitable culture conditions for the production of said PAL polypeptide; and (b) recovering expressed PAL polypeptide.

7. The unicellular host of claim 5 wherein the host cell is selected from the group consisting of E. coli, Pseudomonas, Bacillus, Streptomyces, yeast, CHO, R1.1, B-W, LM, COS-1, COS-7, BSC1, BSC40, BMT10 and SF9 cells.

8. The unicellular host according to claim 7 wherein the unicellular host is a yeast selected from the group consisting of Saccharomyces, Pichia, Candida, Hansenula, and Torulopsis.

9. An expression vector which comprises a polynucleotide according to claims 1, 2, or 3.

10. The expression vector of claim 9 wherein the polynucleotide is operatively associated with an expression control sequence.

11. The expression vector of claim 10 wherein said expression control sequence is selected from the group consisting of the immediate early promoters of human cytomegalovirus (hCMV), early promoters of SV 40, early promoters of adenovirus, early promoters of polyoma virus, late promoters of SV 40, late promoters of vaccinia virus, late promoters of polyoma virus, retroviral LTR, inducible promoters, promoters of the lac system, promoters of the trp system, promoters of the TAC system, promoters of the TRC system, the operators and promoter regions of phage lambda, control regions of fd coat protein, 3-phosphoglycerate kinase promoter, acid phosphatase promoter, and promoters of yeast a mating factor.

12. An isolated mammalian cell containing a polynucleotide encoding a PAL polypeptide comprising the amino acid sequence set out in SEQ ID NO:2 or SEQ ID NO:4, wherein the polynucleotide is modified by means of a homologous recombinational event so as to permit higher expression of the PAL polypeptide, wherein the modification consists of the insertion of an expression regulatory sequence in functional proximity to the polynucleotide encoding the PAL polypeptide.

13. A method for producing a PAL polypeptide, the method comprising the steps of:

(a) culturing a mammalian cell according to claim 12 under suitable culture conditions for the production of said PAL polypeptide; and (b) recovering expressed PAL polypeptide.

14. A diagnostic reagent comprising a detectably labeled polynucleotide encoding the polypeptide sequence set out in SEQ ID NO.:2.

15. A diagnostic reagent comprising detectably labeled polynucleotide encoding the polypeptide set out in SEQ ID NO.:4.

16. The diagnostic reagent of claim 14 or 15 wherein the labeled polynucleotide is a DNA.

17. A diagnostic reagent of claim 14 or 15 wherein the labeled polynucleotide is a first-strand cDNA.

* * * * *

UNITED STATES PATENT AND TRADEMARK OFFICE
CERTIFICATE OF CORRECTION

PATENT NO.    : 6,492,138 B1                                           Page 1 of 1
DATED         : December 10, 2002
INVENTOR(S)   : McGlade et al.

It is certified that error appears in the above-identified patent and that said Letters Patent is hereby corrected as shown below:

Column 51,
Line 12, please delete "Seq. ID. No.: 2 or Seq. ID No.: 4, identity to" and insert -- Seq. ID No.: 2 or Seq. ID No.: 4, or an amino acid sequence having greater than 85% identity to --
Lines 35 and 37, please delete "claims" and insert -- claim --

Column 52,
Line 9, please delete "claims" and insert -- claim --
Line 25, please delete "yeast a mating factor" and insert -- yeast α mating factor --

Signed and Sealed this

Twelfth Day of August, 2003

JAMES E. ROGAN
*Director of the United States Patent and Trademark Office*